(12) United States Patent
Loos

(10) Patent No.: US 6,506,148 B2
(45) Date of Patent: Jan. 14, 2003

(54) NERVOUS SYSTEM MANIPULATION BY ELECTROMAGNETIC FIELDS FROM MONITORS

(76) Inventor: Hendricus G. Loos, 3019 Cresta Way, Laguna Beach, CA (US) 92651

(*) Notice: Subject to any disclaimer, the term of this patent is extended or adjusted under 35 U.S.C. 154(b) by 8 days.

(21) Appl. No.: 09/872,528

(22) Filed: Jun. 1, 2001

(65) Prior Publication Data

US 2002/0188164 A1 Dec. 12, 2002

(51) Int. Cl.[7] .................. A61N 2/00; A61B 5/04; A61M 21/00
(52) U.S. Cl. ........................ 600/27; 600/545
(58) Field of Search ............. 600/9–27, 545; 313/419; 324/318; 378/901; 434/236

(56) References Cited

U.S. PATENT DOCUMENTS

| | | | | |
|---|---|---|---|---|
| 3,592,965 | A | * 7/1971 | Diaz | 313/419 |
| 4,800,893 | A | * 1/1989 | Ross et al. | 600/545 |
| 5,169,380 | A | 12/1992 | Brennan | 600/26 |
| 5,304,112 | A | * 4/1994 | Mrklas et al. | 434/236 |
| 5,400,383 | A | * 3/1995 | Yassa et al. | 378/901 |
| 5,412,419 | A | * 5/1995 | Ziarati | 324/318 |
| 5,450,859 | A | * 9/1995 | Litovitz | 600/9 |
| 5,782,874 | A | 7/1998 | Loos | 607/2 |
| 5,800,481 | A | 9/1998 | Loos | 607/100 |
| 5,899,922 | A | 5/1999 | Loos | 607/2 |
| 5,935,054 | A | 8/1999 | Loos | 600/9 |
| 6,017,302 | A | 1/2000 | Loos | 600/28 |
| 6,081,744 | A | 6/2000 | Loos | 607/2 |
| 6,091,994 | A | 7/2000 | Loos | 607/100 |
| 6,167,304 | A | 12/2000 | Loos | 607/2 |
| 6,238,333 | B1 | 5/2001 | Loos | 600/9 |

OTHER PUBLICATIONS

N.Wiener "Nonlinear problems in random theory" p.71–72 John Wiley New York 1958.
M.Hutchison "Megabrain" p.232–3 Ballantine Books New York 1991.
C.A.Terzuolo and T.H.Bullock "Measurement of imposed voltage gradient adequate to modulate neuronal firing" Proc. Nat. Acad. Sci, Physiology 42,687–94, 1956.
O.Kellogg"Foundations of Potential Theory"p. 191 Dover, 1953.
P.M.Morse and H.Feshbach"Methods of Theoretical Physics"p. 1267 McGraw–Hill New York, 1953.

* cited by examiner

Primary Examiner—Eric F. Winakur
Assistant Examiner—Nikita R Veniaminov

(57) ABSTRACT

Physiological effects have been observed in a human subject in response to stimulation of the skin with weak electromagnetic fields that are pulsed with certain frequencies near ½ Hz or 2.4 Hz, such as to excite a sensory resonance. Many computer monitors and TV tubes, when displaying pulsed images, emit pulsed electromagnetic fields of sufficient amplitudes to cause such excitation. It is therefore possible to manipulate the nervous system of a subject by pulsing images displayed on a nearby computer monitor or TV set. For the latter, the image pulsing may be imbedded in the program material, or it may be overlaid by modulating a video stream, either as an RF signal or as a video signal. The image displayed on a computer monitor may be pulsed effectively by a simple computer program. For certain monitors, pulsed electromagnetic fields capable of exciting sensory resonances in nearby subjects may be generated even as the displayed images are pulsed with subliminal intensity.

14 Claims, 9 Drawing Sheets

FIG.11
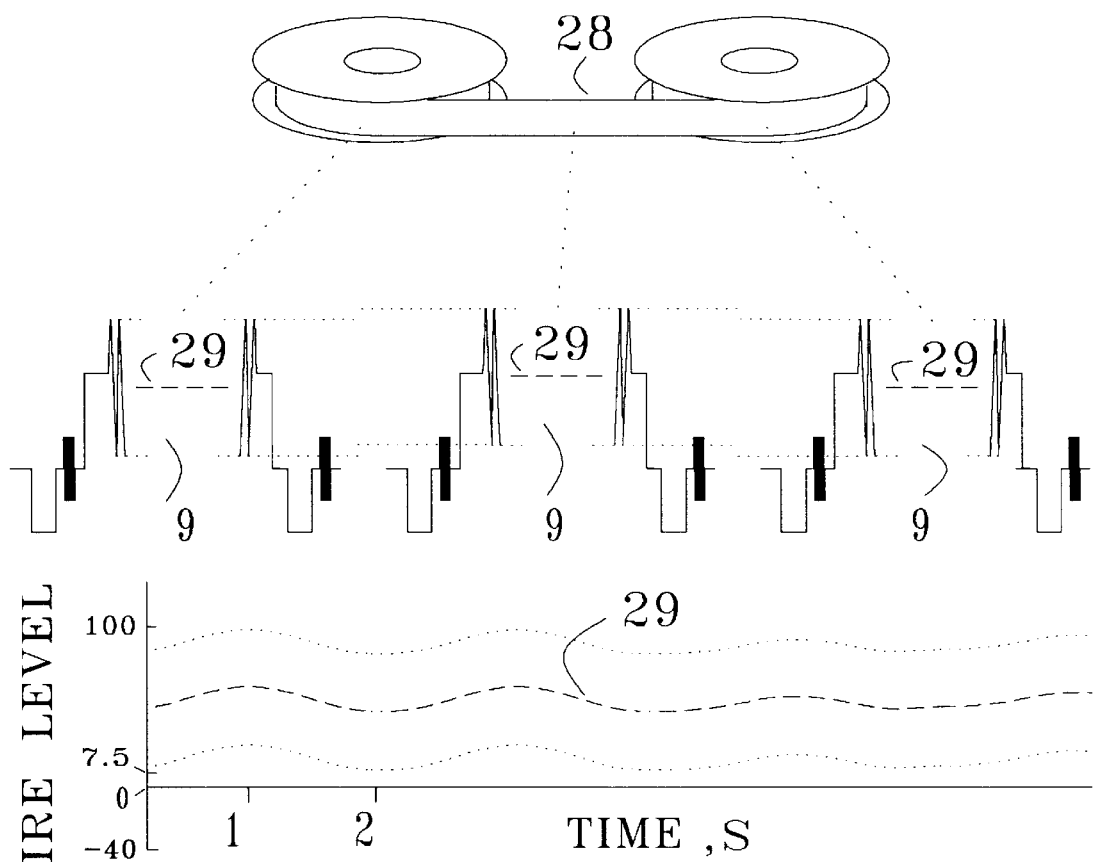
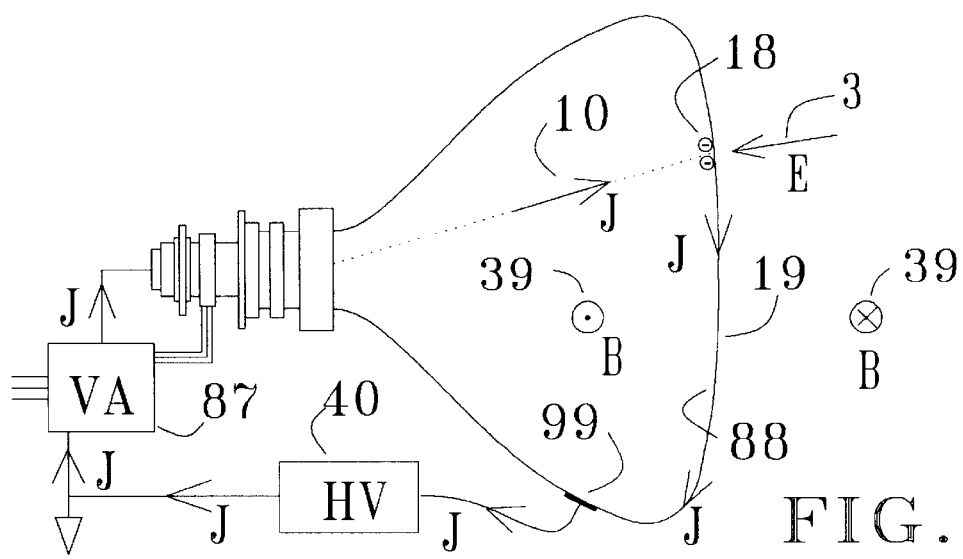
FIG.14

NERVOUS SYSTEM MANIPULATION BY ELECTROMAGNETIC FIELDS FROM MONITORS

BACKGROUND OF THE INVENTION

The invention relates to the stimulation of the human nervous system by an electromagnetic field applied externally to the body. A neurological effect of external electric fields has been mentioned by Wiener (1958), in a discussion of the bunching of brain waves through nonlinear interactions. The electric field was arranged to provide "a direct electrical driving of the brain". Wiener describes the field as set up by a 10 Hz alternating voltage of 400 V applied in a room between ceiling and ground. Brennan (1992) describes in U.S. Pat. No. 5,169,380 an apparatus for alleviating disruptions in circadian rythms of a mammal, in which an alternating electric field is applied across the head of the subject by two electrodes placed a short distance from the skin.

A device involving a field electrode as well as a contact electrode is the "Graham Potentializer" mentioned by Hutchison (1991). This relaxation device uses motion, light and sound as well as an alternating electric field applied mainly to the head. The contact electrode is a metal bar in Ohmic contact with the bare feet of the subject, and the field electrode is a hemispherical metal headpiece placed several inches from the subject's head.

In these three electric stimulation methods the external electric field is applied predominantly to the head, so that electric currents are induced in the brain in the physical manner governed by electrodynamics. Such currents can be largely avoided by applying the field not to the head, but rather to skin areas away from the head. Certain cutaneous receptors may then be stimulated and they would provide a signal input into the brain along the natural pathways of afferent nerves. It has been found that, indeed, physiological effects can be induced in this manner by very weak electric fields, if they are pulsed with a frequency near ½ Hz. The observed effects include ptosis of the eyelids, relaxation, drowziness, the feeling of pressure at a centered spot on the lower edge of the brow, seeing moving patterns of dark purple and greenish yellow with the eyes closed, a tonic smile, a tense feeling in the stomach, sudden loose stool, and sexual excitement, depending on the precise frequency used, and the skin area to which the field is applied. The sharp frequency dependence suggests involvement of a resonance mechanism.

It has been found that the resonance can be excited not only by externally applied pulsed electric fields, as discussed in U.S. Pat. Nos. 5,782,874, 5,899,922, 6,081,744, and 6,167,304, but also by pulsed magnetic fields, as described in U.S. Pat. Nos. 5,935,054 and 6,238,333, by weak heat pulses applied to the skin, as discussed in U.S. Pat. Nos. 5,800,481 and 6,091,994, and by subliminal acoustic pulses, as described in U.S. Pat. No. 6,017,302. Since the resonance is excited through sensory pathways, it is called a sensory resonance. In addition to the resonance near ½ Hz, a sensory resonance has been found near 2.4 Hz. The latter is characterized by the slowing of certain cortical processes, as discussed in the '481, '922, '302, '744, '944, and '304 patents.

The excitation of sensory resonances through weak heat pulses applied to the skin provides a clue about what is going on neurologically. Cutaneous temperature-sensing receptors are known to fire spontaneously. These nerves spike somewhat randomly around an average rate that depends on skin temperature. Weak heat pulses delivered to the skin in periodic fashion will therefore cause a slight frequency modulation (fm) in the spike patterns generated by the nerves. Since stimulation through other sensory modalities results in similar physiological effects, it is believed that frequency modulation of spontaneous afferent neural spiking patterns occurs there as well.

It is instructive to apply this notion to the stimulation by weak electric field pulses administered to the skin. The externally generated fields induce electric current pulses in the underlying tissue, but the current density is much too small for firing an otherwise quiescent nerve. However, in experiments with adapting stretch receptors of the crayfish, Terzuolo and Bullock (1956) have observed that very small electric fields can suffice for modulating the firing of already active nerves. Such a modulation may occur in the electric field stimulation under discussion.

Further understanding may be gained by considering the electric charges that accumulate on the skin as a result of the induced tissue currents. Ignoring thermodynamics, one would expect the accumulated polarization charges to be confined strictly to the outer surface of the skin. But charge density is caused by a slight excess in positive or negative ions, and thermal motion distributes the ions through a thin layer. This implies that the externally applied electric field actually penetrates a short distance into the tissue, instead of stopping abruptly at the outer skin surface. In this manner a considerable fraction of the applied field may be brought to bear on some cutaneous nerve endings, so that a slight modulation of the type noted by Terzuolo and Bullock may indeed occur.

The mentioned physiological effects are observed only when the strength of the electric field on the skin lies in a certain range, called the effective intensity window. There also is a bulk effect, in that weaker fields suffice when the field is applied to a larger skin area. These effects are discussed in detail in the '922 patent.

Since the spontaneous spiking of the nerves is rather random and the frequency modulation induced by the pulsed field is very shallow, the signal to noise ratio (S/N) for the fm signal contained in the spike trains along the afferent nerves is so small as to make recovery of the fm signal from a single nerve fiber impossibile. But application of the field over a large skin area causes simultaneous stimulation of many cutaneous nerves, and the fm modulation is then coherent from nerve to nerve. Therefore, if the afferent signals are somehow summed in the brain, the fm modulations add while the spikes from different nerves mix and interlace. In this manner the S/N can be increased by appropriate neural processing. The matter is discussed in detail in the '874 patent. Another increase in sensitivity is due to involving a resonance mechanism, wherein considerable neural circuit oscillations can result from weak excitations.

An easily detectable physiological effect of an excited ½ Hz sensory resonance is ptosis of the eyelids. As discussed in the '922 patent, the ptosis test involves first closing the eyes about half way. Holding this eyelid position, the eyes are rolled upward, while giving up voluntary control of the eyelids. The eyelid position is then determined by the state of the autonomic nervous system. Furthermore, the pressure excerted on the eyeballs by the partially closed eyelids increases parasympathetic activity. The eyelid position thereby becomes somewhat labile, as manifested by a slight flutter. The labile state is sensitive to very small shifts in autonomic state. The ptosis influences the extent to which the pupil is hooded by the eyelid, and thus how much light is admitted to the eye. Hence, the depth of the ptosis is seen by the subject, and can be graded on a scale from 0 to 10.

In the initial stages of the excitation of the ½ Hz sensory resonance, a downward drift is detected in the ptosis frequency, defined as the stimulation frequency for which maximum ptosis is obtained. This drift is believed to be caused by changes in the chemical milieu of the resonating neural circuits. It is thought that the resonance causes perturbations of chemical concentrations somewhere in the brain, and that these perturbations spread by diffusion to nearby resonating circuits. This effect, called "chemical detuning", can be so strong that ptosis is lost altogether when the stimulation frequency is kept constant in the initial stages of the excitation. Since the stimulation then falls somewhat out of tune, the resonance decreases in amplitude and chemical detuning eventually diminishes. This causes the ptosis frequency to shift back up, so that the stimulation is more in tune and the ptosis can develop again. As a result, for fixed stimulation frequencies in a certain range, the ptosis slowly cycles with a frequency of several minutes. The matter is discussed in the '302 patent.

The stimulation frequencies at which specific physiological effects occur depend somewhat on the autonomic nervous system state, and probably on the endocrine state as well.

Weak magnetic fields that are pulsed with a sensory resonance frequency can induce the same physiological effects as pulsed electric fields. Unlike the latter however, the magnetic fields penetrate biological tissue with nearly undiminished strength. Eddy currents in the tissue drive electric charges to the skin, where the charge distributions are subject to thermal smearing in much the same way as in electric field stimulation, so that the same physiological effects develop. Details are discussed in the '054 patent.

SUMMARY

Computer monotors and TV monitors can be made to emit weak low-frequency electromagnetic fields merely by pulsing the intensity of displayed images. Experiments have shown that the ½ Hz sensory resonance can be excited in this manner in a subject near the monitor. The 2.4 Hz sensory resonance can also be excited in this fashion. Hence, a TV monitor or computer monitor can be used to manipulate the nervous system of nearby people.

The implementations of the invention are adapted to the source of video stream that drives the monitor, be it a computer program, a TV broadcast, a video tape or a digital video disc (DVD).

For a computer monitor, the image pulses can be produced by a suitable computer program. The pulse frequency may be controlled through keyboard input, so that the subject can tune to an individual sensory resonance frequency. The pulse amplitude can be controlled as well in this manner. A program written in Visual Basic(R) is particularly suitable for use on computers that run the Windows 95(R) or Windows 98(R) operating system. The structure of such a program is described. Production of periodic pulses requires an accurate timing procedure. Such a procedure is constructed from the GetTimeCount function available in the Application Program Interface (API) of the Windows operating system, together with an extrapolation procedure that improves the timing accuracy.

Pulse variability can be introduced through software, for the purpose of thwarting habituation of the nervous system to the field stimulation, or when the precise resonance frequency is not known. The variability may be a pseudo-random variation within a narrow interval, or it can take the form of a frequency or amplitude sweep in time. The pulse variability may be under control of the subject.

The program that causes a monitor to display a pulsing image may be run on a remote computer that is connected to the user computer by a link; the latter may partly belong to a network, which may be the Internet.

For a TV monitor, the image pulsing may be inherent in the video stream as it flows from the video source, or else the stream may be modulated such as to overlay the pulsing. In the first case, a live TV broadcast can be arranged to have the feature imbedded simply by slightly pulsing the illumination of the scene that is being broadcast. This method can of course also be used in making movies and recording video tapes and DVDs.

Video tapes can be edited such as to overlay the pulsing by means of modulating hardware. A simple modulator is discussed wherein the luminance signal of composite video is pulsed without affecting the chroma signal. The same effect may be introduced at the consumer end, by modulating the video stream that is produced by the video source. A DVD can be edited through software, by introducing pulse-like variations in the digital RGB signals. Image intensity pulses can be overlaid onto the analog component video output of a DVD player by modulating the luminance signal component. Before entering the TV set, a television signal can be modulated such as to cause pulsing of the image intensity by means of a variable delay line that is connected to a pulse generator.

Certain monitors can emit electromagnetic field pulses that excite a sensory resonance in a nearby subject, through image pulses that are so weak as to be subliminal. This is unfortunate since it opens a way for mischievous application of the invention, whereby people are exposed unknowingly to manipulation of their nervous systems for someone else's purposes. Such application would be unethical and is of course not advocated. It is mentioned here in order to alert the public to the possibility of covert abuse that may occur while being online, or while watching TV, a video, or a DVD.

DESCRIPTION OF THE DRAWINGS

FIG. 11 depicts schematically a recording medium in the form of a video tape with recorded data, and the attribute of the signal that causes the intensity of the displayed image to be pulsed.

FIG. 14 shows schematically how a CRT emits an electromagnetic field when the displayed image is pulsed.

DETAILED DESCRIPTION

Figure 1:
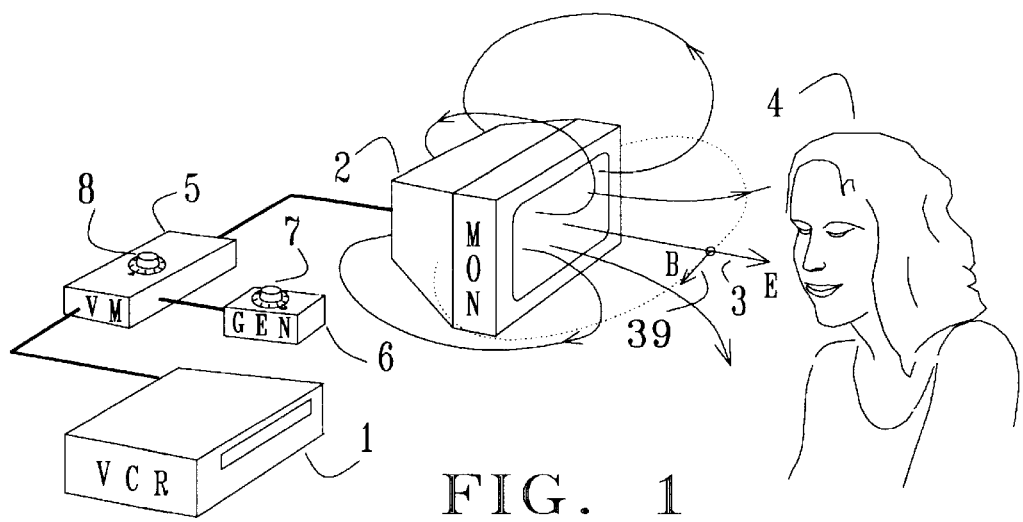
FIG. 1 illustrates the electromagnetic field that emanates from a monitor when the video signal is modulated such as to cause pulses in image intensity, and a nearby subject who is exposed to the field.

Computer monitors and TV monitors emit electromagnetic fields. Part of the emission occurs at the low frequencies at which displayed images are changing. For instance, a rythmic pulsing of the intensity of an image causes electromagnetic field emission at the pulse frequency, with a strength proportional to the pulse amplitude. The field is briefly referred to as "screen emission". In discussing this effect, any part or all what is displayed on the monitor screen is called an image. A monitor of the cathode ray tube (CRT) type has three electron beams, one for each of the basic colors red, green, and blue. The intensity of an image is here defined as $$I = \int j \, dA, \qquad (1)$$

where the integral extends over the image, and $$j = jr + jg + jb, \qquad (2)$$

jr, jg, and jb being the electric current densities in the red, green, and blue electron beams at the surface area dA of the image on the screen. The current densities are to be taken in the distributed electron beam model, where the discreteness of pixels and the raster motion of the beams are ignored, and the back of the monitor screen is thought to be irradiated by diffuse electron beams. The beam current densities are then functions of the coordinates x and y over the screen. The model is appropriate since we are interested in the electromagnetic field emision caused by image pulsing with the very low frequencies of sensory resonances, whereas the emissions with the much higher horizontal and vertical sweep frequencies are of no concern. For a CRT the intensity of an image is expressed in milliamperes.

For a liquid crystal display (LCD), the current densities in the definition of image intensity are to be replaced by driving voltages, multiplied by the aperture ratio of the device. For an LCD, image intensities are thus expressed in volts.

It will be shown that for a CRT or LCD screen emissions are caused by fluctuations in image intensity. In composite video however, intensity as defined above is not a primary signal feature, but luminance Y is. For any pixel one has $$Y = 0.299R + 0.587G + 0.114B, \qquad (3)$$

where R, G, and B are the intensities of the pixel respectively in red, green and blue, normalized such as to range from 0 to 1. The definition (3) was provided by the Commission Internationale de l'Eclairage (CIE), in order to account for brightness differences at different colors, as perceived by the human visual system. In composite video the hue of the pixel is determined by the chroma signal or chrominance, which has the components R-Y and B-Y It follows that pulsing pixel luminance while keeping the hue fixed is equivalent to pulsing the pixel intensity, up to an amplitude factor. This fact will be relied upon when modulating a video stream such as to overlay image intensity pulses.

It turns out that the screen emission has a multipole expansion wherein both monopole and dipole contributions are proportional to the rate of change of the intensity I of (1). The higher order multipole contributions are proportional to the rate of change of moments of the current density j over the image, but since these contributions fall off rapidly with distance, they are not of practical importance in the present context. Pulsing the intensity of an image may involve different pulse amplitudes, frequencies, or phases for different parts of the image. Any or all of these features may be under subject control.

The question arises whether the screen emission can be strong enough to excite sensory resonances in people located at normal viewing distances from the monitor. This turns out to be the case, as shown by sensory resonance experiments and independently by measuring the strength of the emitted electric field pulses and comparing the results with the effective intensity window as explored in earlier work.

One-half Hertz sensory resonance experiments have been conducted with the subject positioned at least at normal viewing distance from a 15" computer monitor that was driven by a computer program written in Visual Basic(R), version 6.0 (VB6). The program produces a pulsed image with uniform luminance and hue over the full screen, except for a few small control buttons and text boxes. In VB6, screen pixel colors are determined by integers R, G, and B, that range from 0 to 255, and set the contributions to the pixel color made by the basic colors red, green, and blue. For a CRT-type monitor, the pixel intensities for the primary colors may depend on the RGB values in a nonlinear manner that will be discussed. In the VB6 program the RGB values are modulated by small pulses $\Delta R$, $\Delta G$, $\Delta B$, with a frequency that can be chosen by the subject or is swept in a predetermined manner. In the sensory resonance experiments mentioned above, the ratios $\Delta R/R$, $\Delta G/G$, and $\Delta B/B$ were always smaller than 0.02, so that the image pulses are quite weak. For certain frequencies near ½ Hz, the subject experienced physiological effects that are known to accompany the excitation of the ½ Hz sensory resonance as mentioned in the Background Section. Moreover, the measured field pulse amplitudes fall within the effective intensity window for the ½ Hz resonance, as explored in earlier experiments and discussed in the '874, '744, '922, and '304 patents. Other experiments have shown that the 2.4 Hz sensory resonance can be exited as well by screen emissions from monitors that display pulsed images.

These results confirm that, indeed, the nervous system of a subject can be manipulated through electromagnetic field pulses emitted by a nearby CRT or LCD monitor which displays images with pulsed intensity.

The various implementations of the invention are adapted to the different sources of video stream, such as video tape, DVD, a computer program, or a TV broadcast through free space or cable. In all of these implementations, the subject is exposed to the pulsed electromagnetic field that is generated by the monitor as the result of image intensity pulsing. Certain cutaneous nerves of the subject exhibit spontaneous spiking in patterns which, although rather random, contain sensory information at least in the form of average frequency. Some of these nerves have receptors that respond to the field stimulation by changing their average spiking frequency, so that the spiking patterns of these nerves acquire a frequency modulation, which is conveyed to the brain. The modulation can be particularly effective if it has a frequency at or near a sensory resonance frequency. Such frequencies are expected to lie in the range from 0.1 to 15 Hz.

An embodiment of the invention adapted to a VCR is shown in FIG. 1, where a subject 4 is exposed to a pulsed electric field 3 and a pulsed magnetic field 39 that are emitted by a monitor 2, labeled "MON", as the result of pulsing the intensity of the displayed image. The image is here generated by a video casette recorder 1, labeled "VCR", and the pulsing of the image intensity is obtained by modulating the composite video signal from the VCR output. This is done by a video modulator 5, labeled "VM", which responds to the signal from the pulse generator 6, labeled "GEN". The frequency and amplitude of the image pulses can be adjusted with the frequency control 7 and amplitude control 8. Frequency and amplitude adjustments can be made by the subject.

Figure 2:
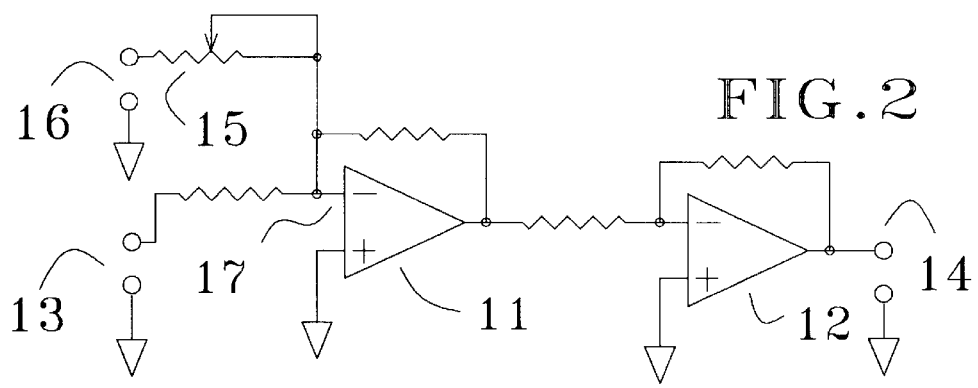
FIG. 2 shows a circuit for modulation of a composite video signal for the purpose of pulsing the image intensity.
Figure 3:
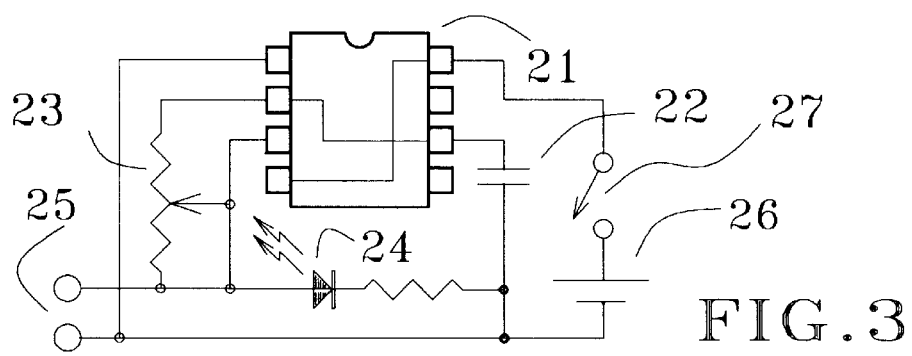
FIG. 3 shows the circuit for a simple pulse generator.

The circuit of the video modulator 5 of FIG. 1 is shown in FIG. 2, where the video amplifiers 11 and 12 process the composite video signal that enters at the input terminal 13. The level of the video signal is modulated slowly by injecting a small bias current at the inverting input 17 of the first amplifier 11. This current is caused by voltage pulses supplied at the modulation input 16, and can be adjusted through the potentiometer 15. Since the noninverting input of the amplifier is grounded, the inverting input 17 is kept essentially at ground potential, so that the bias current is is not influenced by the video signal. The inversion of the signal by the first amplifier 11 is undone by the second amplifier 12. The gains of the amplifiers are chosen such as to give a unity overall gain. A slowly varying current injected at the inverting input 17 causes a slow shift in the "pseudo-dc" level of the composite video signal, here defined as the short-term average of the signal. Since the pseudo-dc level of the chroma signal section determines the luminance, the latter is modulated by the injected current pulses. The chroma signal is not affected by the slow modulation of the pseudodc level, since that signal is determined by the amplitude and phase with respect to the color carrier which is locked to the color burst. The effect on the sync pulses and color bursts is of no consequence either if the injected current pulses are very small, as they are in practice. The modulated composite video signal, available at the output 14 in FIG. 2, will thus exhibit a modulated luminance, whereas the chroma signal is unchanged. In the light of the foregoing discussion about luminance and intensity, it follows that the modulator of FIG. 2 causes a pulsing of the image intensity I. It remains to give an example how the pulse signal at the modulation input 16 may be obtained. FIG. 3 shows a pulse generator that is suitable for this purpose, wherein the RC timer 21 (Intersil ICM7555) is hooked up for astable operation and produces a square wave voltage with a frequency that is determined by capacitor 22 and potentiometer 23. The timer 21 is powered by a battery 26, controlled by the switch 27. The square wave voltage at output 25 drives the LED 24, which may be used for monitoring of the pulse frequency, and also serves as power indicator. The pulse output may be rounded in ways that are well known in the art. In the setup of FIG. 1, the output of VCR 1 is connected to the video input 13 of FIG. 2, and the video output 14 is connected to the monitor 2 of FIG. 1.

Figure 4:
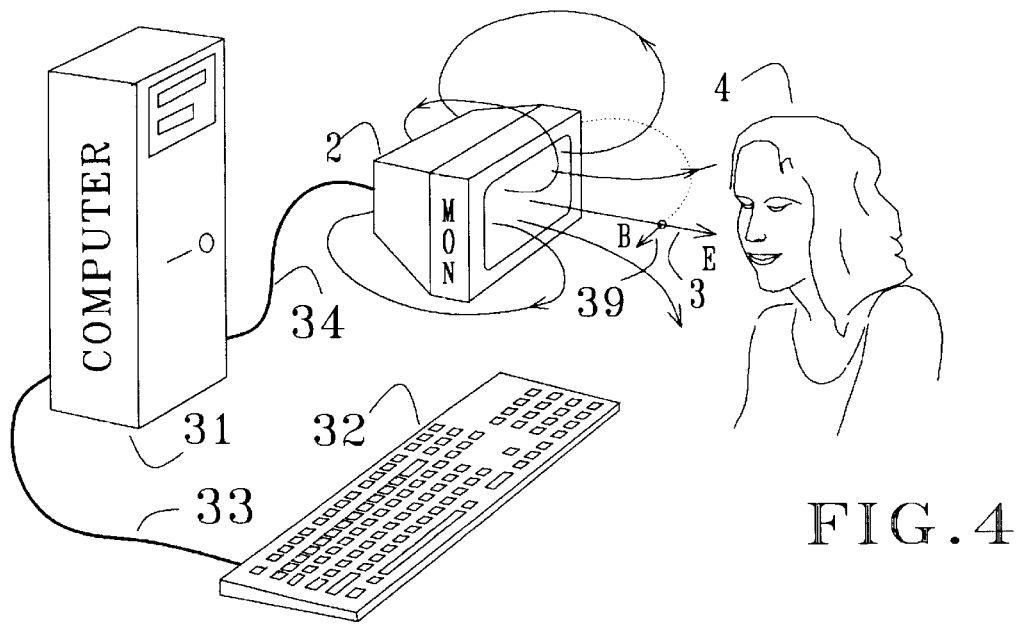
FIG. 4 illustrates how a pulsed electromagnetic field can be generated with a computer monitor.

In the preferred embodiment of the invention, the image intensity pulsing is caused by a computer program. As shown in FIG. 4, monitor 2, labeled "MON", is connected to computer 31 labeled "COMPUTER", which runs a program that produces an image on the monitor and causes the image intensity to be pulsed. The subject 4 can provide input to the computer through the keyboard 32 that is connected to the computer by the connection 33. This input may involve adjustments of the frequency or the amplitude or the variability of the image intensity pulses. In particular, the pulse frequency can be set to a sensory resonance frequency of the subject for the purpose of exciting the resonance.

Figure 6:
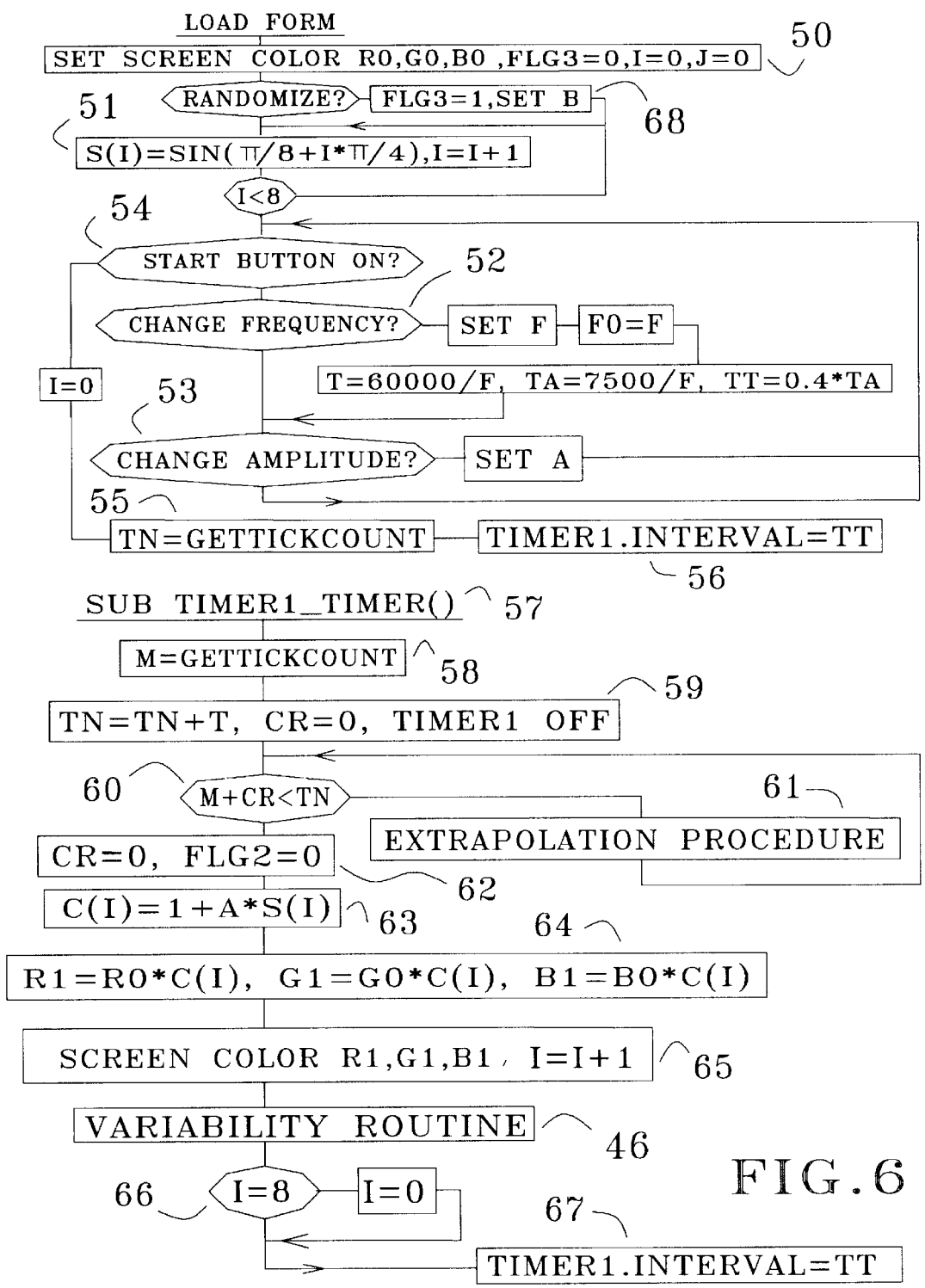
FIG. 6 outlines the structure of a computer program for producing a pulsed image.

The structure of a computer program for pulsing image intensity is shown in FIG. 6. The program may be written in Visual Basic(R) version 6.0 (VB6), which involves the graphics interface familiar from the Windows(R) operating system. The images appear as forms equipped with user controls such as command buttons and scroll bars, together with data displays such as text boxes. A compiled VB6 program is an executable file. When activated, the program declares variables and functions to be called from a dynamic link library (DLL) that is attached to the operating system; an initial form load is performed as well. The latter comprises setting the screen color as specified by integers R, G, and B in the range 0 to 255, as mentioned above. In FIG. 6, the initial setting of the screen color is labeled as 50. Another action of the form load routine is the computation 51 of the sine function at eight equally spaced points, I=0 to 7, around the unit circle. These values are needed when modulating the RGB numbers. Unfortunately, the sine function is distorted by the rounding to integer RGB values that occurs in the VB6 program. The image is chosen to fill as much of the screen area as possible, and it has spatially uniform luminance and hue.

The form appearing on the monitor displays a command button for starting and stopping the image pulsing, together with scroll bars 52 and 53 respectively for adjustment of the pulse frequency F and the pulse amplitude A. These pulses could be initiated by a system timer which is activated upon the elapse of a preset time interval. However, timers in VB6 are too inaccurate for the purpose of providing the eight RGB adjustment points in each pulse cycle. An improvement can be obtained by using the GetTickCount function that is available in the Application Program Interface (API) of Windows 95(R) and Windows 98(R). The GetTickCount function returns the system time that has elapsed since starting Windows, expressed in milliseconds. User activation of the start button 54 provides a tick count TN through request 55 and sets the timer interval to TT miliseconds, in step 56. TT was previously calculated in the frequency routine that is activated by changing the frequency, denoted as step 52.

Since VB6 is an event-driven program, the flow chart for the program falls into disjoint pieces. Upon setting the timer interval to TT in step 56, the timer runs in the background while the program may execute subroutines such as adjustment of pulse frequency or amplitude. Upon elapse of the timer interval TT, the timer subroutine 57 starts execution with request 58 for a tick count, and in 59 an upgrade is computed of the time TN for the next point at which the RGB values are to be adjusted. In step 59 the timer is turned off, to be reactivated later in step 67. Step 59 also resets the parameter CR which plays a role in the extrapolation procedure 61 and the condition 60. For ease of understanding at this point, it is best to pretend that the action of 61 is simply to get a tick count, and to consider the loop controled by condition 60 while keeping CR equal to zero. The loop would terminate when the tick count M reaches or exceeds the time TN for the next phase point, at which time the program should adjust the image intensity through steps 63–65. For now step 62 is to be ignored also, since it has to do with the actual extrapolation procedure 61. The increments to the screen colors R1, G1, and B1 at the new phase point are computed according to the sine function, applied with the amplitude A that was set by the user in step 53. The number I that labels the phase point is incremented by unity in step 65, but if this results in I=8 the value is reset to zero in 66. Finally, the timer is reactivated in step 67, initiating a new ⅛-cycle step in the periodic progression of RGB adjustments.

Figure 7:
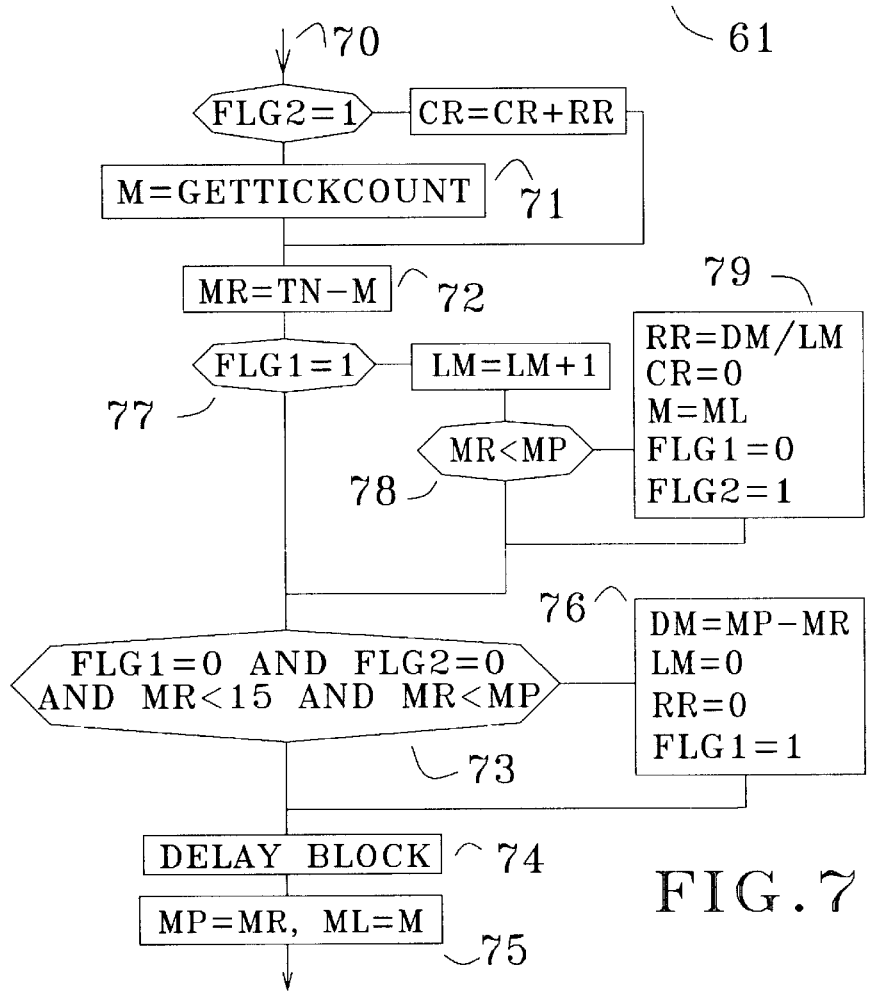
FIG. 7 shows an extrapolation procedure introduced for improving timing accuracy of the program of FIG. 6.
Figure 8:
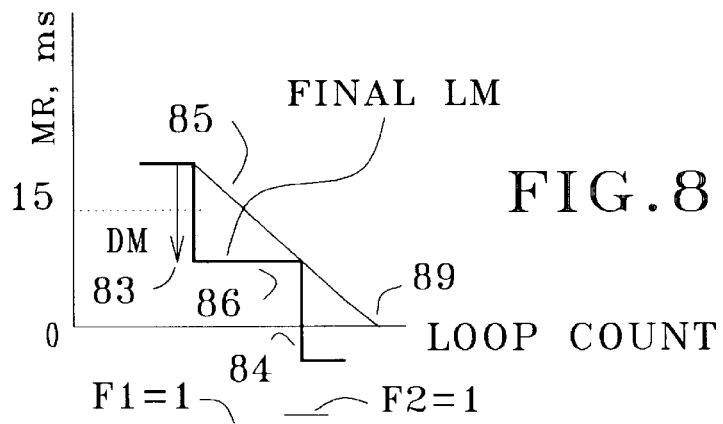
FIG. 8 illustrates the action of the extrapolation procedure of FIG. 7.

A program written in this way would exhibit a large jitter in the times at which the RGB values are changed. This is due to the lumpiness in the tick counts returned by the GetTickCount function. The lumpiness may be studied separately by running a simple loop with C=GetTickCount, followed by writing the result C to a file. Inspection shows that C has jumped every 14 or 15 milliseconds, between long stretches of constant values. Since for a ½ Hz image intensity modulation the ⅛-cycle phase points are 250 ms apart, the lumpiness of 14 or 15 ms in the tick count would cause considerable inaccuracy. The full extrapolation procedure 61 is introduced in order to diminish the jitter to acceptable levels. The procedure works by refining the heavy-line staircase function shown in FIG. 8, using the slope RR of a recent staircase step to accurately determine the loop count 89 at which the loop controled by 60 needs to be exited. Details of the extrapolation procedure are shown in FIG. 7 and illustrated in FIG. 8. The procedure starts at 70 with both flags off, and CR=0, because of the assignment in 59 or 62 in FIG. 6. A tick count M is obtained at 71, and the remaining time MR to the next phase point is computed in 72. Conditions 77 and 73 are not satisfied and therefore passed vertically in the flow chart, so that only the delay block 74 and the assignments 75 are executed. Condition 60 of FIG. 6 is checked and found to be satisfied, so that the extrapolation procedure is reentered. The process is repeated until the condition 73 is met when the remaining time MR jumps down through the 15 ms level, shown in FIG. 8 as the transition 83. The condition 73 then directs the logic flow to the assignments 76, in which the number DM labeled by 83 is computed, and FLG1 is set. The computation of DM is required for finding the slope RR of the straight-line element 85. One also needs the "Final LM" 86, which is the number of loops traversed from step 83 to the next downward step 84, here shown to cross the MR=0 axis. The final LM is determined after repeatedly incrementing LM through the side loop entered from the FLG1=1 condition 77, which is now satisfied since FLG1 was set in step 76. At the transition 84 the condition 78 is met, so that the assignments 79 are executed. This includes computation of the slope RR of the line element 85, setting FLG2, and resetting FLG1. From here on, the extrapolation procedure increments CR in steps of RR while skipping tick counts until condition 60 of FIG. 6 is violated, the loop is exited, and the RGB values are adjusted.

A delay block 74 is used in order to stretch the time required for traversing the extrapolation procedure. The block can be any computation intensive subroutine such as repeated calculations of tangent and arc tangent functions.

As shown in step 56 of FIG. 6, the timer interval TT is set to 4/10 of the time TA from one RGB adjustment point to the next. Since the timer runs in the background, this arrangement provides an opportunity for execution of other processes such as user adjustment of frequency or amplitude of the pulses.

The adjustment of the frequency and other pulse parameters of the image intensity modulation can be made internally, i.e., within the running program. Such internal control is to be distinguished from the external control provided, for instance, in screen savers. In the latter, the frequency of animation can be modified by the user, but only after having exited the screen saver program. Specifically, in Windows 95(R) or Windows 98(R), to change the animation frequency requires stopping the screen saver execution by moving the mouse, whereafter the frequency may be adjusted through the control panel. The requirement that the control be internal sets the present program apart from so-called banners as well.

Figure 9:
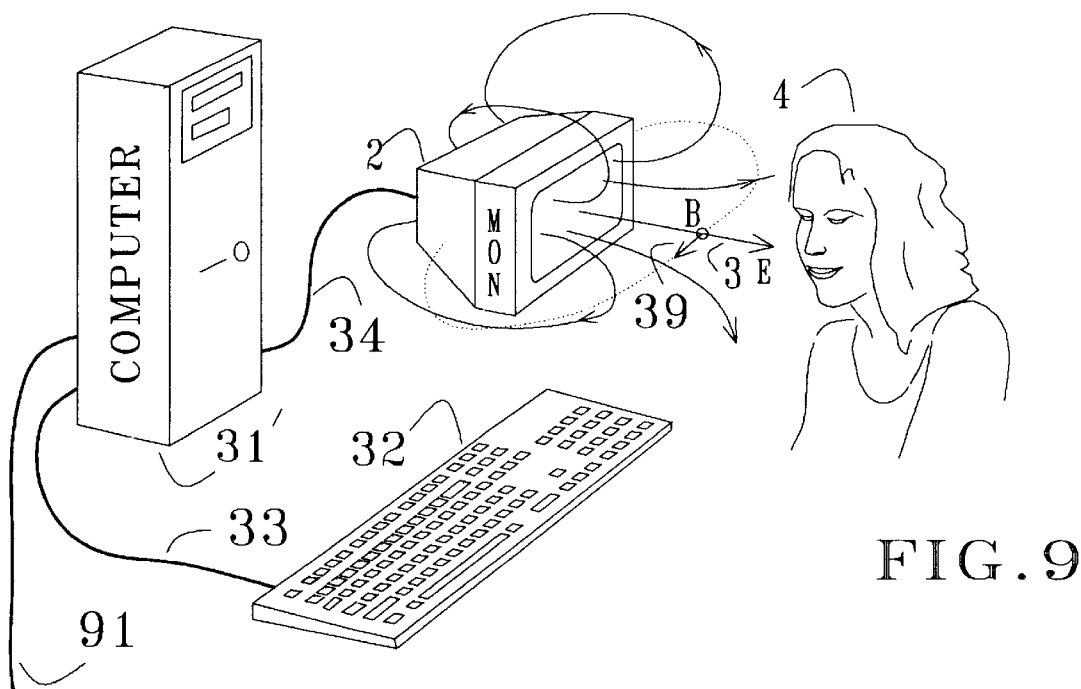
FIG. 9 shows a subject exposed to a pulsed electromagnetic field emanating from a monitor which is responsive to a program running on a remote computer via a link that involves the Internet.

The program may be run on a remote computer that is linked to the user computer, as illustrated in FIG. 9. Although the monitor 2, labeled "MON", is connected to the computer 31', labeled "COMPUTER", the program that pulses the images on the monitor 2 runs on the remoter computer 90, labeled "REMOTE COMPUTER", which is connected to computer 31' through a link 91 which may in part belong to a network. The network may comprise the Internet 92.

Figure 5:
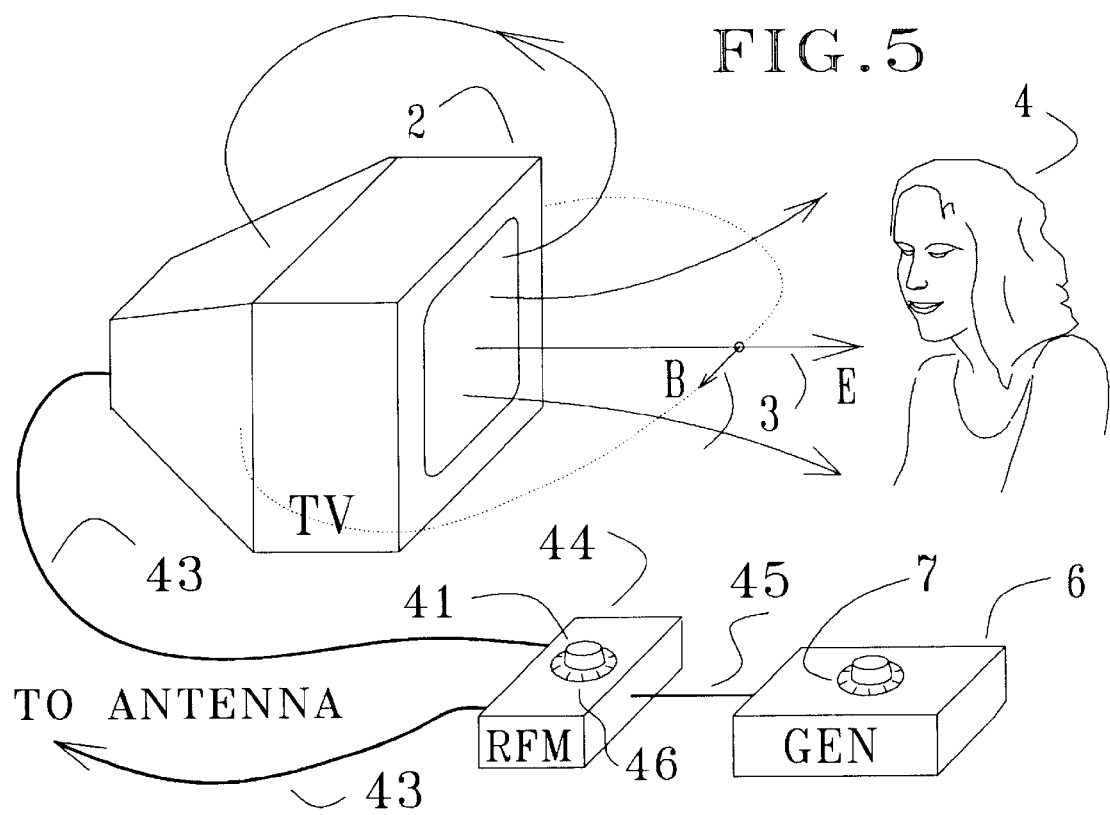
FIG. 5 shows a pulsed electromagnetic field that is generated by a television set through modulation of the RF signal input to the TV.
Figure 10:
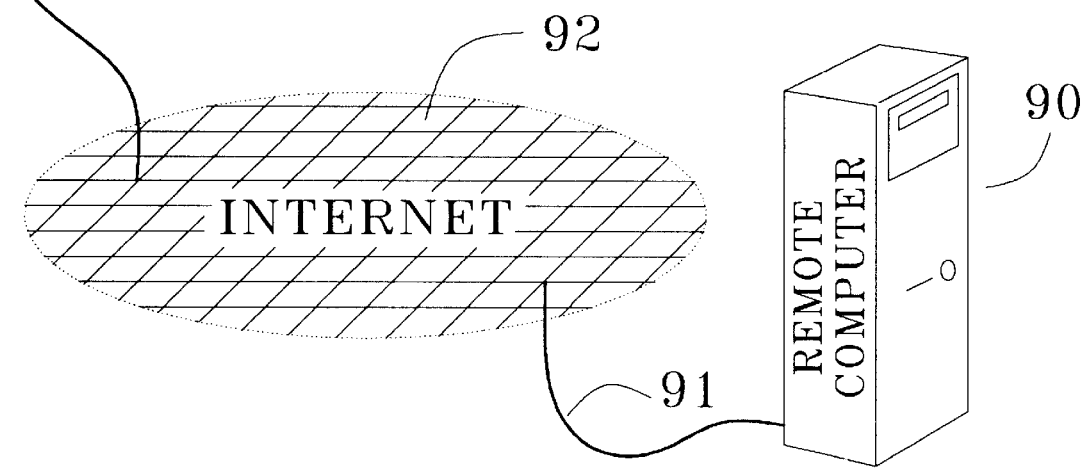
FIG. 10 shows the block diagram of a circuit for frequency wobbling of a TV signal for the purpose of pulsing the intensity of the image displayed on a TV monitor.
Figure 10:
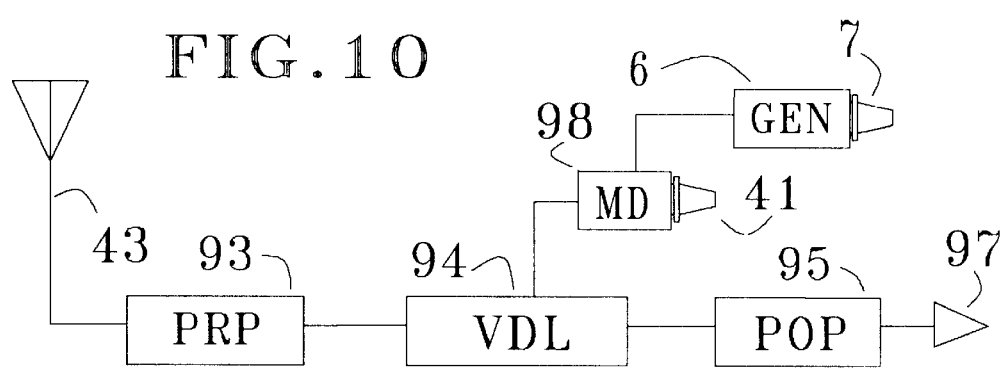

The monitor of a television set emits an electromagnetic field in much the same way as a computer monitor. Hence, a TV may be used to produce screen emissions for the purpose of nervous system manipulation. FIG. 5 shows such an arrangement, where the pulsing of the image intensity is achieved by inducing a small slowly pulsing shift in the frequency of the RF signal that enters from the antenna. This process is here called "frequency wobbling" of the RF signal. In FM TV, a slight slow frequency wobble of the RF signal produces a pseudo-dc signal level fluctuation in the composite video signal, which in turn causes a slight intensity fluctuation of the image displayed on the monitor in the same manner as discussed above for the modulator of FIG. 2. The frequency wobbling is induced by the wobbler 44 of FIG. 5 labeled "RFM", which is placed in the antenna line 43. The wobbler is driven by the pulse generator 6, labeled "GEN". The subject can adjust the frequency and the amplitude of the wobble through the tuning control 7 and the amplitude control 41. FIG. 10 shows a block diagram of the frequency wobbler circuit that employs a variable delay line 94, labelled "VDL". The delay is determined by the signal from pulse generator 6, labelled "GEN". The frequency of the pulses can be adjusted with the tuning control 7. The amplitude of the pulses is determined by the unit 98, labelled "MD", and can be adjusted with the amplitude control 41. Optionally, the input to the delay line may be routed through a preprocessor 93, labelled "PRP", which may comprise a selective RF amplifier and down converter; a complimentary up conversion should then be performed on the delay line output by a postprocessor 95, labelled "POP". The output 97 is to be connected to the antenna terminal of the TV set.

The action of the variable delay line 94 may be understood as follows. Let periodic pulses with period L be presented at the input. For a fixed delay the pulses would emerge at the output with the same period L. Actually, the time delay T is varied slowly, so that it increases approximately by LdT/dt between the emergence of consecutive pulses at the device output. The pulse period is thus increased approximately by $$\Delta L = L dT/dt. \quad (4)$$

In terms of the frequency $f$, Eq. (4) implies approximately $$\Delta f / f = -dT/dt. \quad (5)$$

For sinusoidal delay T(t) with amplitude b and frequency g, one has $$\Delta f / f = -2\pi g b \cos(2\pi g t), \quad (6)$$

which shows the frequency wobbling. The approximation is good for gb<<1, which is satisfied in practice. The relative frequency shift amplitude 2πgb that is required for effective image intensity pulses is very small compared to unity. For a pulse frequency g of the order of 1 Hz, the delay may have to be of the order of a millisecond. To accomodate such long delay values, the delay line may have to be implemented as a digital device. To do so is well within the present art. In that case it is natural to also choose digital implementations for the pulse generator 6 and the pulse amplitude controller 98, either as hardware or as software.

Pulse variability may be introduced for alleviating the need for precise tuning to a resonance frequency. This may be important when sensory resonance frequencies are not precisely known, because of the variation among individuals, or in order to cope with the frequency drift that results from chemical detuning that is discussed in the '874 patent. A field with suitably chosen pulse variability can then be more effective than a fixed frequency field that is out of tune. One may also control tremors and seizures, by interfering with the pathological oscillatory activity of neural circuits that occurs in these disorders. Electromagnetic fields with a pulse variability that results in a narrow spectrum of frequencies around the frequency of the pathological oscillatory activity may then evoke nerve signals that cause phase shifts which diminish or quench the oscillatory activity.

Figure 13:
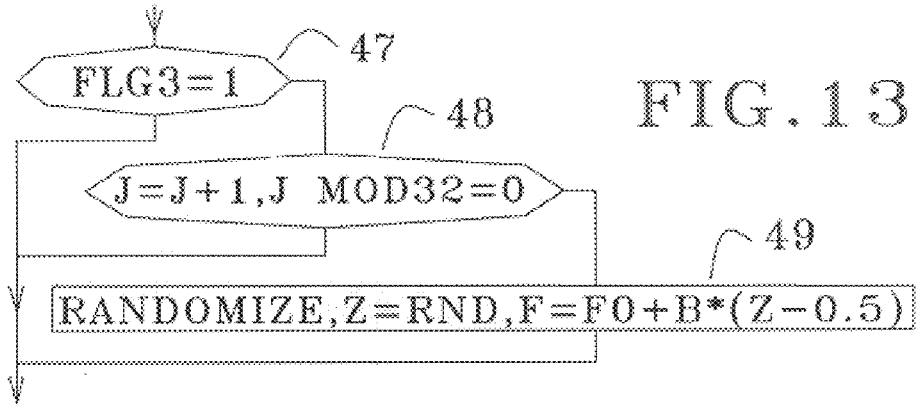
FIG. 13 shows a routine that introduces pulse variability into the computer program of FIG. 6.

Pulse variability can be introduced as hardware in the manner described in the '304 patent. The variability may also be introduced in the computer program of FIG. 6, by setting FLG3 in step 68, and choosing the amplitude B of the frequency fluctuation. In the variability routine 46, shown in some detail in FIG. 13, FLG3 is detected in step 47, whereupon in steps 48 and 49 the pulse frequency F is modified pseudo randomly by a term proportional to B, every 4th cycle. Optionally, the amplitude of the image intensity pulsing may be modified as well, in similar fashion. Alternatively, the frequency and amplitude may be swept through an adjustable ramp, or according to any suitable schedule, in a manner known to those skilled in the art. The pulse variability may be applied to subliminal image intensity pulses.

When an image is displayed by a TV monitor in response to a TV broadcast, intensity pulses of the image may simply be imbedded in the program material. If the source of video signal is a recording medium, the means for pulsing the image intensity may comprise an attribute of recorded data. The pulsing may be subliminal. For the case of a video signal from a VCR, the pertinent data attribute is illustrated in FIG. 11, which shows a video signal record on part of a video tape 28. Depicted schematically are segments of the video signal in intervals belonging to lines in three image frames at different places along the tape. In each segment, the chroma signal 9 is shown, with its short-term average level 29 represented as a dashed line. The short-term average signal level, also called the pseudo-dc level, represents the luminance of the image pixels. Over each segment, the level is here constant because the image is for simplicity chosen as having a uniform luminance over the screen. However, the level is seen to vary from frame to frame, illustrating a luminance that pulses slowly over time. This is shown in the lower portion of the drawing, wherein the IRE level of the short-term chroma signal average is plotted versus time. The graph further shows a gradual decrease of pulse amplitude in time, illustrating that luminance pulse amplitude variations may also be an attribute of the recorded data on the video tape. As discussed, pulsing the luminance for fixed chrominance results in pulsing of the image intensity.

Figure 12:
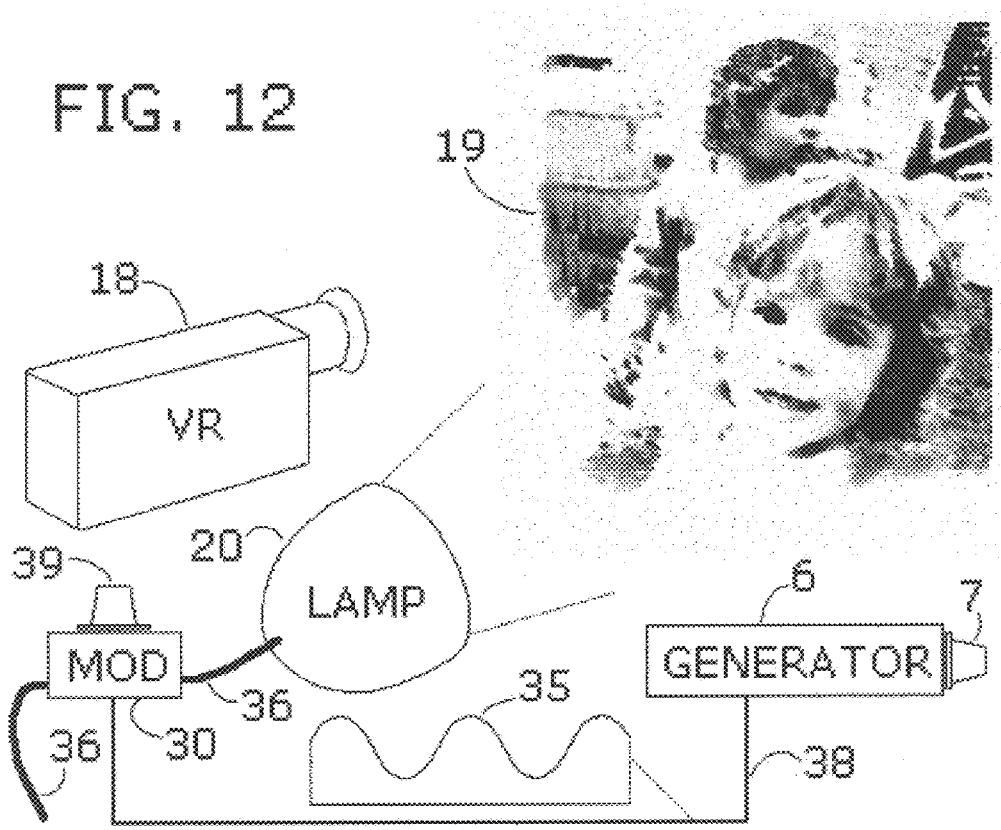
FIG. 12 illustrates how image pulsing can be embedded in a video signal by pulsing the illumination of the scene that is being recorded.

Data stream attributes that represent image intensity pulses on video tape or in TV signals may be created when producing a video rendition or making a moving picture of a scene, simply by pulsing the illumination of the scene. This is illustrated in FIG. 12, which shows a scene 19 that is recorded with a video camera 18, labelled "VR". The scene is illuminated with a lamp 20, labelled "LAMP", energized by an electric current through a cable 36. The current is modulated in pulsing fashion by a modulator 30, labeled "MOD", which is driven by a pulse generator 6, labelled "GENERATOR", that produces voltage pulses 35. Again, pulsing the luminance but not the chrominance amounts to pulsing the image intensity.

Figure 15:
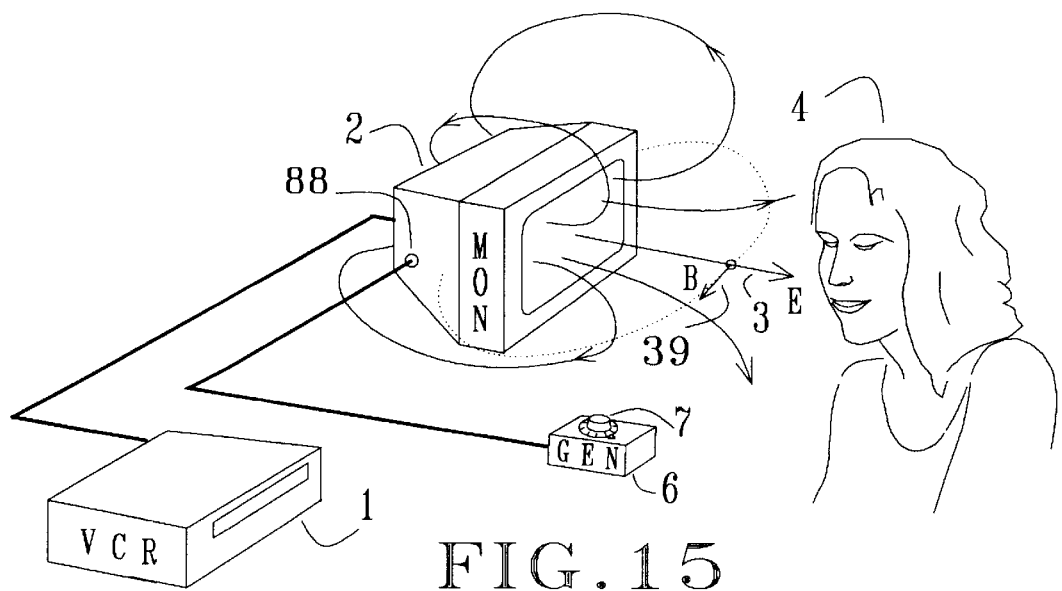
FIG. 15 shows how the intensity of the image displayed on a monitor can be pulsed through the brightness control terminal of the monitor.

The brightness of monitors can usually be adjusted by a control, which may be addressable through a brightness adjustment terminal. If the control is of the analog type, the displayed image intensity may be pulsed as shown in FIG. 15, simply by a pulse generator 6, labeled "GEN", that is connected to the brigthness adjustment terminal 88 of the monitor 2, labeled "MON". Equivalent action can be provided for digital brightness controls, in ways that are well known in the art.

Figure 17:
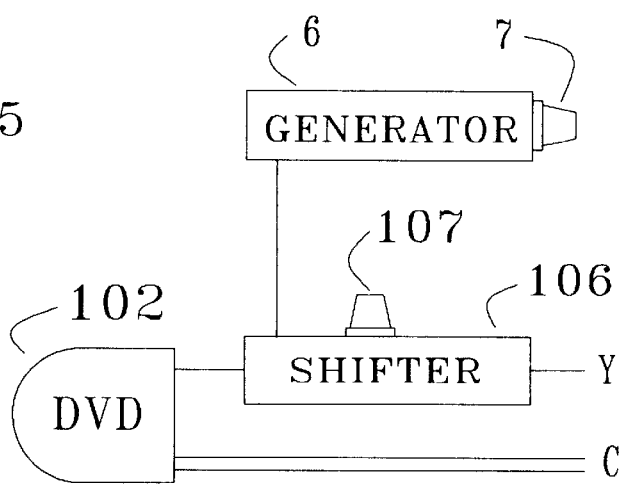
FIG. 17 shows the circuit for overlaying image intensity pulses on a DVD output.

The analog component video signal from a DVD player may be modulated such as to overlay image intensity pulses in the manner illustrated in FIG. 17. Shown are a DVD player 102, labeled "DVD", with analog component video output comprised of the luminance Y and chrominance C. The overlay is accomplished simply by shifting the luminance with a voltage pulse from generator 6, labeled "GENERATOR". The generator output is applied to modulator 106, labeled "SHIFTER". Since the luminance Y is pulsed without changing the chrominance C, the image intensity is pulsed. The frequency and amplitude of the image intensity pulses can be adjusted respectively with the tuner 7 and amplitude control 107. The modulator 105 has the same structure as the modulator of FIG. 2, and the pulse amplitude control 107 operates the potentiometer 15 of FIG. 2. The same procedure can be followed for editing a DVD such as to overlay image intensity pulses, by processing the modulated luminance signal through an analog-to-digital converter, and recording the resulting digital stream onto a DVD, after appropriate compression. Alternatively, the digital luminance data can be edited by electronic reading of the signal, decompression, altering the digital data by software, and recording the resulting digital signal after proper compression, all in a manner that is well known in the art.

The mechanism whereby a CRT-type monitor emits a pulsed electromagnetic field when pulsing the intensity of an image is illustrated in FIG. 14. The image is produced by an electron beam 10 which impinges upon the backside 88 of the screen, where the collisions excite phosphors that subsequently emit light. In the process, the electron beam deposits electrons 18 on the screen, and these electrons contribute to an electric field 3 labelled "E". The electrons flow along the conductive backside 88 of the screen to the terminal 99 which is hooked up to the high-voltage supply 40, labelled "HV". The circuit is completed by the ground connection of the supply, the video amplifier 87, labeled "VA", and its connection to the cathodes of the CRT. The electron beams of the three electron guns are collectively shown as 10, and together the beams carry a current J. The electric current J flowing through the described circuit induces a magnetic field 39, labeled "B". Actually, there are a multitude of circuits along which the electron beam current is returned to the CRT cathodes, since on a macroscopic scale the conductive back surface 88 of the screen provides a continuum of paths from the beam impact point to the high-voltage terminal 99. The magnetic fields induced by the currents along these paths partially cancel each other, and the resulting field depends on the location of the pixel that is addressed. Since the beams sweep over the screen through a raster of horizontal lines, the spectrum of the induced magnetic field contains strong peaks at the horizontal and vertical frequencies. However, the interest here is not in fields at those frequencies, but rather in emissions that result from an image pulsing with the very low frequencies appropriate to sensory resonances. For this purpose a diffuse electron current model suffices, in which the pixel discreteness and the raster motion of the electron beams are ignored, so that the beam current becomes diffuse and fills the cone subtended by the displayed image. The resulting low-frequency magnetic field depends on the temporal changes in the intensity distribution over the displayed image. Order-of-magnitude estimates show that the low-frequency magnetic field, although quite small, may be sufficient for the excitation of sensory resonances in subjects located at a normal viewing distance from the monitor.

The monitor also emits a low-frequency electric field at the image pulsing frequency. This field is due in part to the electrons 18 that are deposited on the screen by the electron beams 10. In the diffuse electron beam model, screen conditions are considered functions of the time t and of the Cartesian coordinates x and y over a flat CRT screen.

The screen electrons 18 that are dumped onto the back of the screen by the sum $j(x,y,t)$ of the diffuse current distributions in the red, green, and blue electron beams cause a potential distribution $V(x,y,t)$ which is influenced by the surface conductivity $\sigma$ on the back of the screen and by capacitances. In the simple model where the screen has a capacitance distribution $c(x,y)$ to ground and mutual capacitances between parts of the screen at different potentials are neglected, a potential distribution $V(x,y,t)$ over the screen implies a surface charge density distribution $$q = V c(x,y), \tag{7}$$

and gives rise to a current density vector along the screen, $$j_s = -\sigma \operatorname{grad}_s V, \tag{8}$$

where $\operatorname{grad}_s$ is the gradient along the screen surface. Conservation of electric charge implies $$j = c\dot{V} - \operatorname{div}_s (\sigma \operatorname{grad}_s V), \tag{9}$$

where the dot over the voltage denotes the time derivative, and $\operatorname{div}_s$ is the divergence in the screen surface. The partial differential equation (9) requires a boundary condition for the solution $V(x,y,t)$ to be unique. Such a condition is provided by setting the potential at the rim of the screen equal to the fixed anode voltage. This is a good approximation, since the resistance $R_r$ between the screen rim and the anode terminal is chosen small in CRT design, in order to keep the voltage loss $JR_r$ to a minimum, and also to limit low-frequency emissions.

Something useful can be learned from special cases with simple solutions. As such, consider a circular CRT screen of radius R with uniform conductivity, showered in the back by a diffuse electron beam with a spatially uniform beam current density that is a constant plus a sinusoidal part with frequency $f$. Since the problem is linear, the voltage V due to the sinusoidal part of the beam current can be considered separately, with the boundary condition that V vanish at the rim of the circular screen. Eq. (9) then simplifies to $$V'' + V'/r - i2\pi f c \eta V = -J\eta/A, \quad r \leq R, \tag{10}$$

where r is a radial coordinate along the screen with its derivative denoted by a prime, $\eta = 1/\sigma$ is the screen resistivity, A the screen area, J the sinusoidal part of the total beam current, and $i = \sqrt{-1}$, the imaginary unit. Our interest is in very low pulse frequencies $f$ that are suitable for excitation of sensory resonances. For those frequencies and for practical ranges for c and $\eta$, the dimensionless number $2\pi f c A \eta$ is very much smaller than unity, so that it can be neglected in Eq. (10). The boundary value problem then has the simple solution $$V(r) = \frac{J\eta}{4\pi}(1 - (r/R)^2). \tag{11}$$

In deriving (11) we neglected the mutual capacitance between parts of the screen that are at different potentials. The resulting error in (10) is negligible for the same reason that the $i2\pi f c A \eta$ term in (10) can be neglected.

Figure 16:
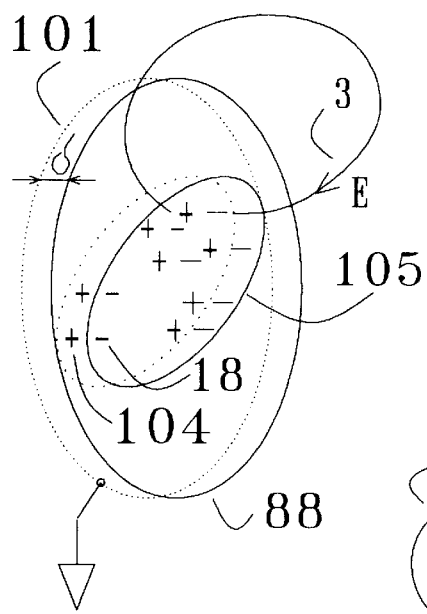
FIG. 16 illustrates the action of the polarization disc that serves as a model for grounded conductors in the back of a CRT screen.

The potential distribution V(r) of (11) along the screen is of course accompanied by electric charges. The field lines emanating from these charges run mainly to conductors behind the screen that belong to the CRT structure and that are either grounded or connected to circuitry with a low impedance path to ground. In either case the mentioned conductors must be considered grounded in the analysis of charges and fields that result from the pulsed component J of the total electron beam current. The described electric field lines end up in electric charges that may be called polarization charges since they are the result of the polarization of the conductors and circuitry by the screen emission. To estimate the pulsed electric field, a model is chosen where the mentioned conductors are represented together as a grounded perfectly conductive disc of radius R, positioned a short distance $\delta$ behind the screen, as depicted in FIG. 16. Since the grounded conductive disc carries polarization charges, it is called the polarization disc. FIG. 16 shows the circular CRT screen 88 and the polarization disc 101, briefly called "plates". For small distances $\delta$, the capacitance density between the plates of opposite polarity is nearly equal to $\epsilon/\delta$, where $\epsilon$ is the permittivity of free space. The charge distributions on the screen and polarization disc are respectively $\epsilon V(r)/\delta + q_0$ and $-\epsilon V(r)/\delta + q_0$, where the $\epsilon V(r)/\delta$ terms denote opposing charge densities at the end of the dense field lines that run between the two plates. That the part $q_0$ is needed as well will become clear in the sequel.

The charge distributions $\epsilon V(r)/\delta + q_0$ and $-\epsilon V(r)/\delta + q_0$ on the two plates have a dipole moment with the density $$D(r) = \epsilon V(r) = \frac{J\eta\epsilon}{4\pi}(1-(r/R)^2), \tag{12}$$

directed perpendicular to the screen. Note that the plate separation δ has dropped out. This means that the precise location of the polarization charges is not critical in the present model, and further that δ may be taken as small as desired. Taking δ to zero, one thus arrives at the mathematical model of pulsed dipoles distributed over the circular CRT screen. The field due to the charge distribution $q_0$ will be calculated later.

The electric field induced by the distributed dipoles (12) can be calculated easily for points on the centerline of the screen, with the result $$E(z) = \frac{V(0)}{R}\{2\rho/R - R/\rho - 2|z|/R\}, \tag{13}$$

where V(0) is the pulse voltage (11) at the screen center, ρ the distance to the rim of the screen, and z the distance to the center of the screen. Note that V(0) pulses harmonically with frequency ʃ, because in (11) the sinusoidal part J of the beam current varies in this manner.

The electric field (13) due to the dipole distribution causes a potential distribution V(r)/2 over the screen and a potential distribution of −V(r)/2 over the polarization disc, where V(r) is nonuniform as given by (11). But since the polarization disc is a perfect conductor it cannot support voltage gradients, and therefore cannot have the potential distribution −V(r)/2. Instead, the polarization disc is at ground potential. This is where the charge distribution $q_0(r)$ comes in; it must be such as to induce a potential distribution V(r)/2 over the polarization disc. Since the distance between polarization disc and screen vanishes in the mathematical model, the potential distribution V(r)/2 is induced over the screen as well. The total potential over the monitor screen thus becomes V(r) of (11), while the total potential distribution over the polarization disc becomes uniformly zero. Both these potential distributions are as physically required. The electric charges $q_0$ are moved into position by polarization and are partly drawn from the earth through the ground connection of the CRT.

In our model the charge distribution $q_0$ is located at the same place as the dipole distribution, viz., on the plane z=0 within the circle with radius R. At points on the center line of the screen, the electric field due to the monopole distribution $q_0$ is calculated in the following manner. As discussed, the monopoles must be such that they cause a potential $\phi_0$ that is equal to V(r)/2 over the disc with radius R centered in the plane z=0. Although the charge distribution $q_0(r)$ is uniquely defined by this condition, it cannot be calculated easily in a straightforward manner. The difficulty is circumvented by using an intermediate result derived from Excercise 2 on page 191 of Kellogg (1953), where the charge distribution over a thin disc with uniform potential is given. By using this result one readily finds the potential $\phi^*(z)$ on the axis of this disc as $$\phi^*(z) = \frac{2}{\pi}V^*\beta(R_1), \tag{14}$$

where $\beta(R_1)$ is the angle subtended by the disc radius $R_1$, as viewed from the point z on the disc axis, and $V^*$ is the disc potential. The result is used here in an attempt to construct the potential $\phi_0(z)$ for a disc with the nonuniform potential V(r)/2, by the ansatz of writing the field as due to a linear combination of abstract discs with various radii $R_1$ and potentials, all centered in the plane z=0. In the ansatz the potential on the symmetry axis is written $$\phi_0(z) = a\beta(R) + b\int_0^R \beta(R_1)dW, \tag{15}$$

where W is chosen as the function $1-R_1^2/R^2$, and the constants a and b are to be determined such that the potential over the plane z=0 is V(r)/2 for radii r ranging from 0 to R, with V(r) given by (11). Carrying out the integration in (15) gives $$\phi_0(z) = a\beta(R) - b\{(1+z^2/R^2)\beta(R) - |z|/R\}. \tag{16}$$

In order to find the potential over the disc r<R in the plane z=0, the function $\phi_0(z)$ is expanded in powers of z/R for 0<z<R, whereafter the powers $z^n$ are replaced by $r^nP_n(\cos\theta)$, where the $P_n$ are Legendre polynomials, and (r,θ) are symmetric spherical coordinates centered at the screen center. This procedure amounts to a continuation of the potential from the z-axis into the half ball r<R, z>0, in such a manner that the Laplace equation is satisfied. The method is discussed by Morse and Feshbach (1953). The "Laplace continuation" allows calculation of the potential $\phi_0$ along the surface of the disc r<R centered in the plane z=0. The requirement that this potential be V(r)/2 with the function V(r) given by (11) allows solving for the constants a and b, with the result $$a=-V(0)/\pi, \; b=-2V(0)/\pi. \tag{17}$$

Using (17) in (16) gives $$\phi_0(z) = \frac{V(0)}{\pi}[(1+2z^2/R^2)\beta(R) - 2|z|/R], \tag{18}$$

and by differentiation with respect to z one finally finds $$E_0(z) = \frac{V(0)}{\pi R}(z/|z|)[4 - (R/\rho)^2 - 4\beta(R)|z|/R] \tag{19}$$

for the electric field on the center line of the screen brought about by the charge distribution $q_0(z)$.

The center-line electric field is the sum of the part (13) due to distributed pulsed dipoles and part (19) due to distributed pulsed monopoles. Although derived for circular screens, the results may serve as an approximation for other shapes, such as the familiar rounded rectangle, by taking R as the radius of a circle that has the same area as the screen.

Figure 18:
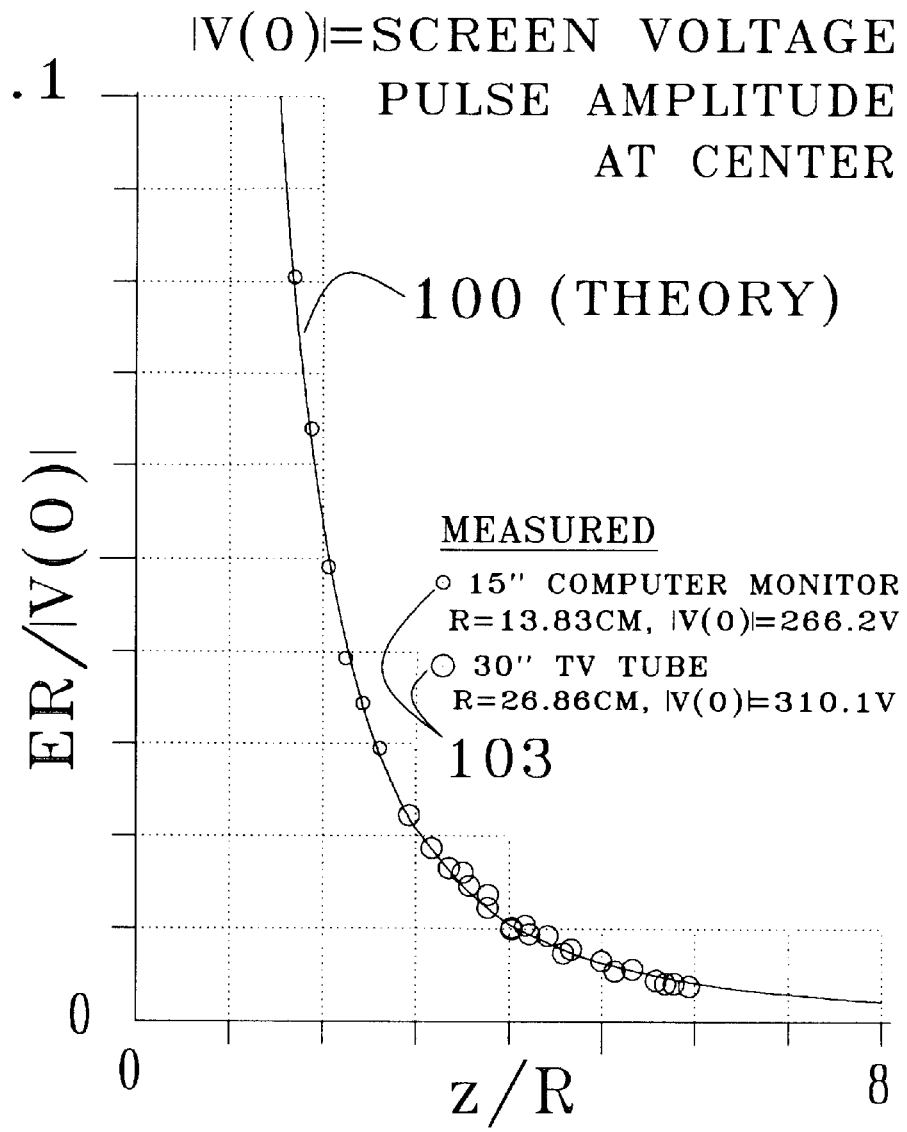
FIG. 18 shows measured data for pulsed electric fields emitted by two different CRT type monitors, and a comparison with theory.

For two CRT-type monitors the pulsed electric field due to image intensity pulsing has been measured at several points on the screen center line for pulse frequencies of ½ Hz. The monitors were the 15" computer monitor used in the sensory resonance experiments mentioned above, and a 30" TV tube. The experimental results need to be compared with the theory derived above. Since R is determined by the screen area, the electric fields given by (13) and (19) have as only free parameter the pulse voltage V(0) at the screen center. The amplitude of this voltage can therefore be determined for the tested monitors by fitting the experimental data to the theoretical results. Prior to fitting, the data were normalized to an image that occupies the entire screen and is pulsed uniformly with a 100% intensity amplitude. The results of the one-parameter fit are displayed in FIG. 18, which shows the theoretical graph 100, together with the normalized experimental data points 103 for the 15″ computer monitor and for the 30″ TV tube. FIG. 18 shows that the developed theory agrees fairly well with the experimental results. From the best fit one can find the center-screen voltage pulse amplitudes. The results, normalized as discussed above, are $|V(0)|=266.2$ volt for the 15″ computer monitor and $|V(0)|=310.1$ volt for the 30″ TV tube. With these amplitudes in hand, the emitted pulsed electric field along the center line of the monitors can be calculated from the sum of the fields (13) and (19). For instance, for the 15″ computer monitor with 1.8% RGB pulse modulation used in the ½ Hz sensory resonance experiments mentioned above, the pulsed electric field at the center of the subject, located at z=70 cm on the screen center line, is calculated as having an amplitude of 0.21 V/m. That such a pulsed electric field, applied to a large portion of the skin, is sufficient for exciting the ½ Hz sensory resonance is consistent with experimental results discussed in the '874 patent.

In deriving (11), the dimensionless number $2\pi \int cA\eta$ was said to be much smaller than unity. Now that the values for $|V(0)|$ are known, the validity of this statement can be checked. Eq. (11) implies that $|V(0)|$ is equal to $\eta|J|/4\pi$. The sum of the beam currents in the red, green, and blue electron guns for 100% intensity modulation is estimated to have pulse amplitudes $|J|$ of 0.5 mA and 2.0 mA respectively for the 15″ computer monitor and the 30″ TV tube. Using the derived values for $|V(0)|$, one arrives at estimates for the screen resistivity $\eta$ as 6.7 M$\Omega$/square and 1.9 M$\Omega$/square respectively for the 15″ computer monitor and the 30″ TV tube. Estimating the screen capacity cA as 7 pf and 13 pf, $2\pi \int cA\eta$ is found to be $148 \times 10^{-6}$ and $78 \times 10^{-6}$, respectively for the 15″ computer monitor and the 30″ TV tube. These numbers are very small compared to unity, so that the step from (10) to (11) is valid.

The following procedures were followed in preparing pulsed images for the field measurements. For the 15″ computer monitor the images were produced by running the VB6 program discussed above. The pulsed image comprised the full screen with basic RGB values chosen uniformly as R=G=B=127, with the exception of an on/off button and a few data boxes which together take up 17% of the screen area. The image intensity was pulsed by modifying the R, G, and B values by integer-rounded sine functions $\Delta R(t)$, $\Delta G(t)$, and $\Delta B(t)$, uniformly over the image, except at the button and the data boxes. The measured electric field pulse amplitudes were normalized to a pulsed image that occupies all of the screen area and has 100% intensity modulation for which the image pulses between black and the maximum intensity, for the fixed RGB ratios used. The image intensity depends on the RGB values in a nonlinear manner that will be discussed. For the measurements of the pulsed electric field emitted by 30″ TV tube, a similar image was used as for the 15″ computer monitor. This was done by playing back a camcorder recording of the computer monitor display when running the VB6 program, with 40% pulse modulation of R, G, and B.

In front of the monitor, i.e., for z>0, the parts (13) and (19) contribute about equally to the electric field over a practical range of distances z. When going behind the monitor where z is negative the monopole field flips sign so that the two parts nearly cancel each other, and the resulting field is very small. Therefore, in the back of the CRT, errors due to imperfections in the theory are relatively large. Moreover our model, which pretends that the polarization charges are all located on the polarization disc, fails to account for the electric field flux that escapes from the outer regions of the back of the screen to the earth or whatever conductors happen to be present in the vincinity of the CRT. This flaw has relatively more serious consequences in the back than in front of the monitor.

Screen emissions in front of a CRT can be cut dramatically by using a grounded conductive transparent shield that is placed over the screen or applied as a coating. Along the lines of our model, the shield amounts to a polarization disc in front of the screen, so that the latter is now sandwiched between to grounded discs. The screen has the pulsed potential distribution V(r) of (11), but no electric flux can escape. The model may be modified by choosing the polarization disc in the back somewhat smaller than the screen disc, by a fraction that serves as a free parameter. The fraction may then be determined from a fit to measured fields, by minimizing the relative standard deviation between experiment and theory.

In each of the electron beams of a CRT, the beam current is a nonlinear function of the driving voltage, i.e., the voltage between cathode and control grid. Since this function is needed in the normalization procedure, it was measured for the 15″ computer monitor that has been used in the ½ Hz sensory resonance experiments and the electric field measurements. Although the beam current density j can be determined, it is easier to measure the luminance, by reading a light meter that is brought right up to the monitor screen. With the RGB values in the VB6 program taken as the same integer K, the luminance of a uniform image is proportional to the image intensity I. The luminance of a uniform image was measured for various values of K. The results were fitted with $$I = c_1 K^\gamma, \qquad (20)$$

where $c_1$ is a constant. The best fit, with 6.18% relative standard deviation, was obtained for $\gamma=2.32$.

Screen emissions also occur for liquid crystal displays (LCD). The pulsed electric fields may have considerable amplitude for LCDs that have their driving electrodes on opposite sides of the liquid crystal cell, for passive matrix as well as for active matrix design, such as thin film technology (TFT). For arrangements with in-plane switching (IPS) however, the driving electrodes are positioned in a single plane, so that the screen emission is very small. For arrangements other than IPS, the electric field is closely approximated by the fringe field of a two-plate condenser, for the simple case that the image is uniform and extends over the full screen. For a circular LCD screen with radius R, the field on the center line can be readily calculated as due to pulsed dipoles that are uniformly distributed over the screen, with the result $$E_d(z) = (\tfrac{1}{2}) V R^2 / (z^2 + R^2)^{3/2}, \qquad (21)$$

where $E_d(z)$ is the amplitude of the pulsed electric field at a distance z from the screen and V is a voltage pulse amplitude, in which the aperture ratio of the LCD has been taken into account. Eq. (21) can be used as an approximation for screens of any shape, by taking R as the radius of a circle with the same area as the screen. The result applies to the case that the LCD does not have a ground connection, so that the top and bottom electrodes are at opposite potential, i.e., V/2 and −V/2.

If one set of LCD electrodes is grounded, monopoles are needed to keep these electrodes at zero potential, much as in the case of a CRT discussed above. The LCD situation is simpler however, as there is no charge injection by electron beams, so that the potentials on the top and bottom plates of the condenser in the model are spatially uniform. From (14)

it is seen that monopoles, distributed over the disc of radius R in the plane z=0 such as to provide on the disc a potential V/2, induce on the symmetry axis a potential $$\phi(z) = \frac{1}{\pi} V \beta(R). \tag{22}$$

Differentiating with respect to z gives the electric field on the symmetry axis $$E_m(z) = \frac{zVR}{|z|\pi(z^2 + R^2)}, \tag{23}$$

induced by the pulsed monopoles. For an LCD with one set of electrodes grounded, the pulsed electric field for screen voltage pulse amplitude V at a distance z from the screen on the center line has an amplitude that is the sum of the parts (21) and (23). The resultant electric field in the back is relatively small, due to the change in sign in the monopole field that is caused by the factor $z/|z|$. Therefore, screen emissions in front of an LCD can be kept small simply by having the grounded electrodes in front.

As a check on the theory, the pulsed electric field emitted by the 3" LCD-TFT color screen of the camcorder mentioned above has been measured at eleven points on the center line of the screen, ranging from 4.0 cm to 7.5 cm. The pulsed image was produced by playing back the video recording of the 15" computer monitor that was made while running the VB6 program discussed above, for a image intensity pulse frequency of ½ Hz, R=G=B=K, modulated around K=127 with an amplitude ΔK=51. After normalization to a uniform full screen image with 100% intensity modulation by using the nonlinear relation (20), the experimental data were fitted to the theoretical curve that expresses the sum of the fields (21) and (23). The effective screen pulse voltage amplitude V was found to be 2.1 volt. The relative standard deviation in V for the fit is 5.1%, which shows that theory and experiment are in fairly good agreement.

Certain monitors can cause excitation of sensory resonances even when the pulsing of displayed images is subliminal, i.e., unnoticed by the average person. When checking this condition on a computer monitor, a problem arises because of the rounding of RGB values to integers, as occurs in the VB6 program. For small pulse amplitude the sine wave is thereby distorted into a square wave, which is easier to spot. This problem is alleviated somewhat by choosing ΔR=0, ΔG=0, and ΔB=2, since then the 8 rounded sine functions around the unit circle, multiplied with the pulse amplitude ΔB=2 become the sequence 1, 2 11 2, 1, −1 −2, −2, −1, etc, which is smoother to the eye than a square wave. Using the VB6 program and the 15" computer monitor mentioned above with R=71, G=71, and B=233, a ½ Hz pulse modulation with amplitudes ΔR=ΔG=0 and ΔB=2 could not be noticed by the subject, and is therefore considered subliminal. It is of interest to calculate the screen emission for this case, and conduct a sensory resonance experiment as well. A distance z=60 cm was chosen for the calculation and the experiment. Using Eq. (20), the image intensity pulse modulation for the case is found to be 1.0% of the maximum intensity modulation. Using R=13.83 cm together with $|V(0)|$=266.2 V for the 15" computer monitor, and the theoretical graph 100 of FIG. 18, the pulsed electric field at z=60 cm was found to have an amplitude of 138 mV/m. In view of the experimental results discussed in the '874 and '922 patents, such a field, used at a pulse frequency chosen appropriately for the ½ Hz sensory resonance and applied predominantly to the face, is expected to be sufficient for exciting the ½ Hz sensory resonance. A confirmation experiment was done by running the VB6 program with the discussed settings and the 15" monitor. The center of the subject's face was positioned on the screen center line, at a distance of 60 cm from the screen. A frequency sweep of −0.1% per ten cycles was chosen, with an initial pulse frequency of 34 ppm. Full ptosis was experienced by the subject at 20 minutes into the run, when the pulse frequency was f=31.76 ppm. At 27 minutes into the run, the frequency sweep was reversed to +0.1% per ten cycles. Full ptosis was experienced at f=31.66 ppm. At 40 minutes into the run, the frequency sweep was set to −0.1% per ten cycles. Full ptosis occurred at f=31.44 ppm. The small differences in ptosis frequency are attributed to chemical detuning, discussed in the Background Section. It is concluded that the ½ Hz sensory resonance was excited in this experiment by screen emissions from subliminal image pulsing on the 15" computer monitor at a distance of 60 cm. For each implementation and embodiment discussed, the image pulsing may be subliminal.

The human eye is less sensitive to changes in hue than to changes in brightness. In composite video this fact allows using a chrominance bandwidth that is smaller than the luminance bandwidth. But it also has the consequence that pulsing of the chrominance for fixed luminance allows larger pulse amplitudes while staying within the subliminal pulse regime. Eq. (3) shows how to pulse the chrominance components R−Y and B−Y while keeping Y fixed; for the change in pixel intensity one then has $$\Delta I_h = 0.491\Delta(R-Y) + 0.806\Delta(B-Y). \tag{24}$$

Luminance pulses with fixed chrominance give a change in pixel intensity $$\Delta I_1 = 3\Delta Y. \tag{25}$$

Of course, pure chrominance pulses may be combined with pure luminance pulses; an instance of such combination has been mentioned above.

The subliminal region in color space needs to be explored to determine how marginally subliminal pulses ΔR, ΔG, and ΔB depend on RGB values. Prior to this, the condition for image pulses to be subliminal should not be phrased solely in terms of the percentage of intensity pulse amplitude. The subliminal image pulsing case considered above, where the monitor is driven by a VB6 computer program with R=G= 71, B=233, and ΔR=ΔG=0, ΔB=2 for full-screen images will be referred to as "the standard subliminal image pulsing".

In the interest of the public we need to know the viewing distances at which a TV with subliminally pulsed images can cause excitation of sensory resonances. A rough exploration is reported here which may serve as starting point for further work. The exploration is limited to estimating the largest distance $z=z_{max}$ along the center line of the 30" TV at which screen emissions can excite the ½ Hz resonance, as determined by the ptosis test. The TV is to display an image which undergoes the standard subliminal pulsing as defined above. It would be best to perform this test with the 30" TV on which the subliminally pulsed images are produced by means of a video. Since such a video was not available, the ptosis test was conducted instead with a pulsed electric field source consisting of a small grounded doublet electrode of the type discussed in the '874 patent. The doublet was driven with a sinusoidal voltage of 10 V amplitude, and the center of mass of the subject was located on the center line of the doublet at a distance $z=z_d$=323 cm. The doublet electrodes are rectangles of 4.4 cm by 4.7 cm. At the large distance $z_d$ there is whole-body exposure to the field, so that the bulk effect discussed in the '874 patent comes into play, as is expected to happen also at the distance $z_{max}$ from the 30" TV monitor. The subject was facing the "hot" electrode of the doublet, so that at the subject center the electric field was the sum of the parts (21) and (23), for positive values of z. It was thought important to use a sine wave, since that would be the "commercially" preferred pulse shape which allows larger pulse amplitudes without being noticed. The only readily available sine wave generator with the required voltage was an oscillator with a rather coarse frequency control that cannot be set accurately, although the frequency is quite stable and can be measured accurately. For the experiment a pulse frequency of 0.506 Hz was accepted, although it differs considerably from the steady ptosis frequency for this case. The subject experienced several ptosis cycles of moderate intensity, starting 8 minutes into the experiment run. It is concluded that the ½ Hz sensory resonance was excited, and that the stimulating field was close to the weakest field capable of excitation. From Eqs. (21) and (23), the electric field pulse amplitude at the center of mass of the subject was found to be 7.9 mV/m. That an electric field with such a small pulse amplitude, applied to the whole body, is capable of exciting the ½ Hz sensory resonance is consistent with experimental results reported in the '874 patent, although these were obtained for the 2.4 Hz resonance. Next, the distance $z_{max}$ was determined at which the 30" TV tube with 1% image intensity pulse amplitude produces an electric field with a pulse amplitude of 7.9 mV/m, along the center line of the screen. From Eqs. (13) and (19) one finds $z_{max}$=362.9 cm. At more than 11 feet, this is a rather large distance for viewing a 30" TV. Yet, the experiment and theory discussed show that the ½ Hz sensory resonance can be excited at this large distance, by pulsing the image intensity subliminally. Of course, the excitation occurs as well for a range of smaller viewing distances. It is thus apparent that the human nervous system can be manipulated by screen emissions from subliminal TV image pulses.

Windows 95, Windows 98, and Visual Basic are registered trademarks of Microsoft Corporation.

The invention is not limited by the embodiments shown in the drawings and described in the specification, which are given by way of example and not of limitation, but only in accordance with the scope of the appended claims.

I claim:

1. A method for manipulating the nervous system of a subject located near a monitor, the monitor emitting an electromagnetic field when displaying an image by virtue of the physical display process, the subject having a sensory resonance frequency, the method comprising:

creating a video signal for displaying an image on the monitor, the image having an intensity;

modulating the video signal for pulsing the image intensity with a frequency in the range 0.1 Hz to 15 Hz; and setting the pulse frequency to the resonance frequency.

2. A computer program for manipulating the nervous system of a subject located near a monitor, the monitor emitting an electromagnetic field when displaying an image by virtue of the physical display process, the subject having cutaneous nerves that fire spontaneously and have spiking patterns, the computer program comprising:

a display routine for displaying an image on the monitor, the image having an intensity;

a pulse routine for pulsing the image intensity with a frequency in the range 0.1 Hz to 15 Hz; and a frequency routine that can be internally controlled by the subject, for setting the frequency;

whereby the emitted electromagnetic field is pulsed, the cutaneous nerves are exposed to the pulsed electromagnetic field, and the spiking patterns of the nerves acquire a frequency modulation.

3. The computer program of claim 2, wherein the pulsing has an amplitude and the program further comprises an amplitude routine for control of the amplitude by the subject.

4. The computer program of claim 2, wherein the pulse routine comprises:

a timing procedure for timing the pulsing; and an extrapolation procedure for improving the accuracy of the timing procedure.

5. The computer program of claim 2, further comprising a variability routine for introducing variability in the pulsing.

6. Hardware means for manipulating the nervous system of a subject located near a monitor, the monitor being responsive to a video stream and emitting an electromagnetic field when displaying an image by virtue of the physical display process, the image having an intensity, the subject having cutaneous nerves that fire spontaneously and have spiking patterns, the hardware means comprising:

pulse generator for generating voltage pulses;

means, responsive to the voltage pulses, for modulating the video stream to pulse the image intensity;

whereby the emitted electromagnetic field is pulsed, the cutaneous nerves are exposed to the pulsed electromagnetic field, and the spiking patterns of the nerves acquire a frequency modulation.

7. The hardware means of claim 6, wherein the video stream is a composite video signal that has a pseudo-dc level, and the means for modulating the video stream comprise means for pulsing the pseudo-dc level.

8. The hardware means of claim 6, wherein the video stream is a television broadcast signal, and the means for modulating the video stream comprise means for frequency wobbling of the television broadcast signal.

9. The hardware means of claim 6, wherein the monitor has a brightness adjustment terminal, and the means for modulating the video stream comprise a connection from the pulse generator to the brightness adjustment terminal.

10. A source of video stream for manipulating the nervous system of a subject located near a monitor, the monitor emitting an electromagnetic field when displaying an image by virtue of the physical display process, the subject having cutaneous nerves that fire spontaneously and have spiking patterns, the source of video stream comprising:

means for defining an image on the monitor, the image having an intensity; and means for subliminally pulsing the image intensity with a frequency in the range 0.1 Hz to 15 Hz;

whereby the emitted electromagnetic field is pulsed, the cutaneous nerves are exposed to the pulsed electromagnetic field, and the spiking patterns of the nerves acquire a frequency modulation.

11. The source of video stream of claim 10 wherein the source is a recording medium that has recorded data, and the means for subliminally pulsing the image intensity comprise an attribute of the recorded data.

12. The source of video stream of claim 10 wherein the source is a computer program, and the means for subliminally pulsing the image intensity comprise a pulse routine.

13. The source of video stream of claim 10 wherein the source is a recording of a physical scene, and the means for subliminally pulsing the image intensity comprise:

pulse generator for generating voltage pulses;

light source for illuminating the scene, the light source having a power level; and modulation means, responsive to the voltage pulses, for pulsing the power level.

14. The source of video stream of claim 10, wherein the source is a DVD, the video stream comprises a luminance signal and a chrominance signal, and the means for subliminal pulsing of the image intensity comprise means for pulsing the luminance signal.

* * * * *